(12) United States Patent
Schroder

(10) Patent No.: US 10,669,595 B2
(45) Date of Patent: Jun. 2, 2020

(54) OLIGONUCLEOTIDE PRIMER COMPOSITION

(71) Applicant: GEN-PROBE INCORPORATED, San Diego, CA (US)

(72) Inventor: Astrid R. W. Schroder, Encinitas, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 451 days.

(21) Appl. No.: 15/377,638

(22) Filed: Dec. 13, 2016

(65) Prior Publication Data

US 2017/0088906 A1    Mar. 30, 2017

Related U.S. Application Data

(63) Continuation of application No. 13/678,317, filed on Nov. 15, 2012, now Pat. No. 9,523,133, which is a continuation of application No. 13/245,483, filed on Sep. 26, 2011, now abandoned, which is a continuation of application No. 11/240,046, filed on Sep. 30, 2005, now abandoned.

(60) Provisional application No. 60/615,533, filed on Sep. 30, 2004.

(51) Int. Cl.
   *C12Q 1/68*     (2018.01)
   *C12Q 1/70*     (2006.01)
   *C12Q 1/6851*   (2018.01)
   *C12Q 1/6865*   (2018.01)

(52) U.S. Cl.
   CPC ........... *C12Q 1/703* (2013.01); *C12Q 1/6851* (2013.01); *C12Q 1/6865* (2013.01); *C12Q 2600/156* (2013.01)

(58) Field of Classification Search
   None
   See application file for complete search history.

(56) References Cited

U.S. PATENT DOCUMENTS

| | | | |
|---|---|---|---|
| 5,457,027 A | 10/1995 | Nadeau et al. | |
| 6,294,338 B1 * | 9/2001 | Nunomura | C12Q 1/6851 435/5 |
| 6,361,945 B1 | 3/2002 | Becker et al. | |
| 6,531,276 B1 | 3/2003 | Luciw et al. | |
| 7,618,642 B2 | 11/2009 | zur Megede et al. | |

(Continued)

FOREIGN PATENT DOCUMENTS

| | | |
|---|---|---|
| EP | 0 774 518 A2 | 5/1997 |
| EP | 1 223 227 A2 | 7/2002 |
| EP | 1 285 971 A2 | 2/2003 |

(Continued)

OTHER PUBLICATIONS

Amendola et al., "Comparison of LCx with Other Current Viral Load Assays for Detecting and Quantifying Human Immunodeficiency Virus Type 1 RNA in Patients Infected with the Circulating Recombinant Form A/G/ (CFRO2)," J. Clin. Microbiol., 2004, 42(2):811-815, ASM, Washington, D.C., USA.

(Continued)

*Primary Examiner* — Stephanie K Mummert
(74) *Attorney, Agent, or Firm* — Michael J. Gilly

(57) ABSTRACT

Oligonucleotide primer useful for synthesizing a cDNA copy of HIV-1 nucleic acids from a broad range of HIV-1 subtypes, including M group and O group variants.

5 Claims, 8 Drawing Sheets

Specification includes a Sequence Listing.

(56) References Cited

U.S. PATENT DOCUMENTS

2002/0150880 A1 10/2002 Hellyer et al.
2006/0286587 A1 12/2006 Lee et al.

FOREIGN PATENT DOCUMENTS

| EP | 1 422 298 A2 | 5/2004 |
|---|---|---|
| WO | 00/01850 A2 | 1/2000 |
| WO | 00/46403 A2 | 8/2000 |
| WO | 01/04361 A2 | 1/2001 |
| WO | 01/07661 A2 | 2/2001 |
| WO | 01/36442 A1 | 5/2001 |
| WO | 02/083927 A2 | 10/2002 |
| WO | 03/020878 A2 | 3/2003 |
| WO | 03/106714 A1 | 12/2003 |

OTHER PUBLICATIONS

Bor et al., "Simultaneous quantitation of several mRNA species by calibrated reverse transcription polymerase chain reaction and capillary electrophoresis: analysis of the epidermal growth factor receptor and its activating ligands EGF, TGF-alpha, and HB-EGF in rat liver," Lab Invest., 2000, 89(6):983-986.
Buck et al., "Design strategies and performance of custom DNA sequencing primers," Biotechniques, 1999, 27 (3):528-536.
Christopherson et al., "The effects of internal primer-template mismatches on RT-PCR: HIV-1 model studies," Nucleic Acids Res., 1997, 25(3):654-658, Oxford University Press, Oxford, United Kingdom.
Database Genbank, Accession No. AC156521, Version No. AC156521.3, "Bos taurus clone CH240-54O23, Working raft Sequence, 9 unordered pieces," Jan. 30, 2005.
De Baar et al., "Single rapid real-time monitored isothermal RNA amplification assay for quantification of human Immunodeficiency virus type 1 isolates from groups M, N, and O," J. Clin. microbiol., 2001, 39(4):1378-1384.
Ghosh e al., "A Molecular Clone of HIV-1 Tropic and Cytopathic for Human and Chimpanzee Lymphocytes," Virology, 1993, 194:858-864, Academic Press, Inc., USA.
Linnen et al., "Sensitive detection of genetic variants of HIV-1 and HCV with an HIV-1/HCV assay based on transcription-mediated amplification," J. Virol. Meths., 2002, 102:139-155, Elsevier, USA.
Lowe et al., "A computer program for selection of oligonucleotide primers for polymerase chain reactions," Nucleic Acids Res., 1990, 18(7):1757-1761, Oxford University Press, Oxford, United Kingdom.
Muller-Trutwin et al., "Towards improvements in molecular tools for diagnosis and management of HIV Infections," The Lancet, 1999, 354:1660-1662, Lancet Ltd., UK.
Peter et al., "Molecular-Based Methods for Quantifying HIV Viral Load," AIDS Patient Care & STDs, 2004, 18 (2):75-79, Mary Ann Liebert, Inc., New Rochelle, NY, USA.
Swanson et al., "Quantification of HIV-1 group M (subtypes A-G) and group O by the LCx HIV RNA quantitative assay," J. Virol. Meths., 2000, 89:97-108, Elsevier, USA.
Takahoko et al., "Infectious DNA clone of HIV type 1 A/G recombinant (CRF02_AG) replicable in peripheral blood mononuclear cells," AIDS Res. Hum. Retroviruses., 2001, 17(11)1083-1087.
Zhang et al., "Differential priming of RNA templates during cDNA synthesis markedly affects both accuracy and reproducibility of quantitative competitive reverse-transcriptase PCR," Biochem. J., 1999, 337:231-241, Biochemical Society, UK.
Zhang et al., Cultured HIV-1, Group M, Subtype A, Gen-Bank Accession No. AY699008, Jul. 26, 2004.
PCT Written Opinion, International Application No. PCT/US2005/035318, dated Nov. 26, 2007.
PCT Search Report, International Application No. PCT/US2005/035318, dated Nov. 26, 2007.
PCT International Preliminary Report on Patentability, International Application No. PCT/US2005/035318, dated Jan. 3, 2008.
APO Patent Examination Report, Australian Patent Application No. 2005291899, dated Feb. 22, 2010.
APO Patent Examination Report, Australian Patent Application No. 2011253599, dated Aug. 17, 2012.
APO Patent Examination Report No. 1, Australian Patent Application No. 2014201154, dated Feb. 25, 2015.
CIPO Office Action, Canadian Patent Application No. 2,847,930, dated Jun. 30, 2014.
CIPO Office Action, Canadian Patent Application No. 2,847,930, dated Mar. 31, 2015.
CIPO Office Action, Canadian Patent Application No. 2,582,055, dated Feb. 28, 2012.
CIPO Notice of Allowance, Canadian Patent Application No. 2,582,055, dated Jan. 9, 2014.
EPO Search Report, European Patent Application No. 05 802 966.1, dated Aug. 13, 2009.
EPO Communication Pursuant to Article 94(3) EPC, European Patent Application No. 05802966.1, dated Oct. 15, 2013.
EPO Extended Search Report, European Patent Application No. 15167734.1, dated Nov. 23, 2015.
JPO Office Action, Japanese Patent Application No. 2007-534923, dated Jun. 16, 2011.
JPO Notice of Final Rejection, Japanese Patent Application No. 2007-534823, dated Jun. 1, 2012.
JPO Office Action, Japanese Patent Application No. 2007-534823, dated Apr. 9, 2014.
USPTO Office Action, U.S. Appl. No. 111240,046, dated Nov. 13, 2007.
USPTO Final Office Action, U.S. Appl. No. 11/240,046, dated Nov. 8, 2008.
USPTO Office Action, U.S. Appl. No. 11/240,046, dated Apr. 16, 2009.
USPTO Office Action, U.S. Appl. No. 11/240,046, dated Feb. 8, 2010.
USPTO Final Office Action, U.S. Appl. No. 11/240,046, dated Aug. 11, 2008.
USPTO Final Office Action, U.S. Appl. No. 11/240,046, dated Oct. 29, 2010.
USPTO Office Action, U.S. Appl. No. 13/245,483, dated Jun. 15, 2012.

* cited by examiner

OLIGONUCLEOTIDE PRIMER COMPOSITION

RELATED APPLICATIONS

This application is a continuation of U.S. application Ser. No. 13/678,317, filed Nov. 15, 2012, now pending, which is a continuation of U.S. application Ser. No. 13/245,483, filed Sep. 26, 2011, now abandoned, which is a continuation of U.S. application Ser. No. 11/240,046, filed Sep. 30, 2005, now abandoned, which claims the benefit of U.S. Provisional Application No. 60/615,533, filed Sep. 30, 2004, the contents of each of which applications is hereby incorporated by reference herein in its entirety.

FIELD

The present invention relates to the field of biotechnology. More specifically, the invention relates to diagnostic assays for detecting and quantifying the nucleic acids of HIV-1.

BACKGROUND

Advances in the clinical management of individuals infected with the human immunodeficiency virus type 1 (HIV-1) have been able to reduce viral titers below the detection limits of some early-generation HIV-1 assays. More specifically, highly active anti-retroviral drug therapy (HAART) can reduce the viral load down to a level approaching 50 HIV-1 RNA copies/ml, a level substantially below the 400-500 copies/ml threshold of some previous detection assays. This fact, together with a desire to monitor and maintain low viral titers, necessitated the development of improved quantitative assays for measuring HIV-1 RNA. (Elbeik et al., *J. Clin. Micro.* 38:1113-1120 (2000)) Complicating matters, however, is the fact that useful quantitative assays must be capable of accurately measuring a range of genetically diverse HIV-1 variants.

Three classes of HIV-1 have developed across the globe: M (major), O (outlying) and N (new). Among the M group, which accounts for greater than 90% of reported HIV/AIDS cases, viral envelopes have diversified so greatly that this group has been subclassified into nine major clades including A-D, F-H, J and K, as well as several circulating recombinant forms. Subtypes within the HIV-1 O group are not clearly defined, and the diversity of sequences within the O group is nearly as great as the diversity of sequences in the HIV-1 M group. Phylogenetic analyses of the gag and env genes have failed to reveal clades of O group viruses as clearly as the clades detected in the M group. Subtypes and sub-subtypes of the HIV-1 M group are thought to have diverged in humans following a single chimpanzee-to-human transmission event. In contrast, the HIV-1 O and N groups are each thought to have resulted from separate chimpanzee-to-human transmission events. Of the completely sequenced HIV-1 genomes, nearly 20% have a mosaic structure consisting of at least two subtypes, yet another potential complication for ultrasensitive HIV-1 detection assays. (Spica et al., *J. Antimicrobial Chemotherapy* 51:229 (2003).)

Most viral load monitoring is currently performed in the developed Western World where the Glade B (i.e., "subtype B" hereafter), which represents only about 3% of HIV infections worldwide, predominates. Importantly, the HIV-1 viral subtypes are expanding in different geographical regions, thereby imposing an additional requirement for broad detection capacity on detection and viral load monitoring assays. Accordingly, there is a need for ultrasensitive HIV-1 detection assays which are capable of accurately measuring the full range of HIV-1 subtypes. The present invention addresses this need.

An example quantitative HIV-1 assay, performed using real-time monitoring of a nucleic acid amplification reaction, has been described in published International Patent Application WO 2003106714.

SUMMARY

A first aspect of the invention relates to a reaction mixture useful for amplifying either HIV-1 M group nucleic acids or HIV-1 O group nucleic acids. The invented reaction mixture ordinarily includes first and second amplification primers. The first amplification primer includes a first primer target-hybridizing sequence that can independently hybridize to a first strand of HIV-1 M group nucleic acids, and to a first strand of HIV-1 O group nucleic acids. The second amplification primer includes a second primer target-hybridizing sequence that hybridizes to an enzymatic extension product of the first amplification primer using as a template either the first strand of HIV-1 M group nucleic acids or the first strand of HIV-1 O group nucleic acids. The second primer target-hybridizing sequence consists essentially of SEQ ID NO:33. In a preferred embodiment, the second primer target-hybridizing sequence consists essentially of SEQ ID NO:2. When this is the case, the first primer target-hybridizing sequence may consist essentially of SEQ ID NO:13. Alternatively, the first primer target-hybridizing sequence may consist essentially of SEQ ID NO:15. In a different preferred embodiment, the second primer target-hybridizing sequence consists essentially of SEQ ID NO:5. When this is the case, the first primer target-hybridizing sequence may consist essentially of SEQ ID NO:15. In yet another preferred embodiment, the reaction mixture further includes a hybridization probe. In some instances, the hybridization probe is a molecular beacon hybridization probe or a molecular torch hybridization probe. Regardless of whether the hybridization probe is a molecular beacon or a molecular torch, it is preferred in certain embodiments that no more than two primers and a single probe are used for amplifying and detecting the HIV-1 M group nucleic acids or the HIV-1 O group nucleic acids.

A second aspect of the invention relates to a method of quantifying the combined amount of an HIV-1 M group nucleic acid and an HIV-1 O group nucleic acid that may be present in a biological sample. The invented method involves steps for: (a) combining in a single reaction vessel the biological sample, a first amplification primer, a second amplification primer, and a hybridization probe; (b) amplifying, with substantially equal efficiency, any of the HIV-1 M group nucleic acid and the HIV-1 O group nucleic acid present in the biological sample using an in vitro amplification reaction that relies on enzymatic extension of the first amplification primer using a first strand of the HIV-1 M group nucleic acid or the HIV-1 O group nucleic acid as a first template to create a first primer extension product, and enzymatic extension of the second amplification primer using the first primer extension product as a second template, whereby there are produced HIV-1 M group amplicons if the biological sample contained HIV-1 M group nucleic acids, and HIV-1 O group amplicons if the biological sample contained HIV-1 O group nucleic acids; (c) monitoring amplicon production in the in vitro amplification reaction as a function of time by a process that includes detection of a signal from the hybridization probe, whereby time-dependent quantitative data is obtained; and (d) quantifying the combined amount of the HIV-1 M group nucleic acid and the HIV-1 O group nucleic acid present in the biological sample using the time-dependent quantitative data obtained in the monitoring step. In accordance with this aspect of the invention, neither the first amplification primer nor the second amplification primer is fully complementary to the HIV-1 M group nucleic acid or the complement thereof, or to the HIV-1 O group nucleic acid or the complement thereof. Further in accordance with this aspect of the invention, the hybridization probe hybridizes to both HIV-1 M group amplicons and HIV-1 O group amplicons. Notably, the invented method also is contemplated for use in detecting and quantifying HIV-1 N group nucleic acids. In a preferred embodiment, the in vitro amplification reaction is an isothermal in vitro amplification reaction that does not require temperature cycling to achieve some degree of exponential amplification. More preferably, the isothermal in vitro amplification reaction is a transcription associated amplification reaction that is either a TMA reaction or a NASBA reaction. In an alternative preferred embodiment, the signal detected in the monitoring step is a fluorescent signal, such as a fluorescent signal produced by a molecular torch hybridization probe. In a highly preferred embodiment, the first amplification primer includes a first primer target-hybridizing sequence that consists essentially of SEQ ID NO:15. More preferably, the second amplification primer includes a second primer target-hybridizing sequence that consists essentially of SEQ ID NO:5. In accordance with another preferred embodiment, no more than two primers and a single probe are used for amplifying and detecting both the HIV-1 M group nucleic acid and the HIV-1 O group nucleic acid. In a highly preferred embodiment, the in vitro amplification reaction is an isothermal in vitro amplification reaction. In an alternative highly preferred embodiment, the quantifying step involves comparing a quantitative result with no more than a single standard curve.

A third aspect of the invention relates to a method of establishing a point on a standard curve that can be used for quantifying HIV-1 M group nucleic acids and HIV-1 O group nucleic acids in a single reaction. The invented method involves steps for: (a) providing a known amount of an HIV-1 standard; (b) amplifying in an in vitro amplification reaction the HIV-1 standard using a first primer and a second primer in the presence of a hybridization probe to produce HIV-1 standard amplicons, wherein the amplification reaction amplifies HIV-1 M group nucleic acids and HIV-1 O group nucleic acids with substantially equal efficiency; (c) monitoring production of HIV-1 standard amplicons synthesized in the in vitro amplification reaction as a function of time by a process that involves detection of a signal from the hybridization probe, whereby quantitative data is obtained; and (d) establishing from the quantitative data a point on the standard curve. In a preferred embodiment, the first amplification primer includes a first primer target-hybridizing sequence that independently hybridizes to a first strand of HIV-1 M group nucleic acids and to a first strand of HIV-1 O group nucleic acids, wherein the second amplification primer includes a second primer target-hybridizing sequence that hybridizes to an enzymatic extension product of the first amplification primer using as a template either the first strand of HIV-1 M group nucleic acids or the first strand of HIV-1 O group nucleic acids. In accordance with this embodiment, (a) neither the first primer target-hybridizing sequence nor the second primer target-hybridizing sequence is fully complementary to HIV-1 M group or HIV-1 O group nucleic acids or the complements thereof, and (b) the hybridization probe is able to hybridize either to HIV-1 M group nucleic acids and HIV-1 O group nucleic acids, or to their complements. In one preferred embodiment, the hybridization probe is a molecular torch. More preferably, when the hybridization probe is a molecular torch, the HIV-1 standard is an HIV-1 M group nucleic acid standard. Still more preferably, when the hybridization probe is a molecular torch, and when the HIV-1 standard is an HIV-1 M group nucleic acid standard, there can be an additional step for using the standard curve to quantify an HIV-1 O group nucleic acid contained in a biological sample. In a different preferred embodiment, the HIV-1 standard is an HIV-1 O group nucleic acid standard. When this is the case, there can be a further step for using the standard curve to quantify an HIV-1 M group nucleic acid contained in a biological sample. In still another different embodiment, the in vitro amplification reaction in the amplifying step can be an isothermal in vitro amplification reaction. When this is the case, the isothermal in vitro amplification reaction can be a transcription associated amplification reaction, such as a TMA reaction or a NASBA reaction. In such an instance, the step for monitoring can involve measuring a fluorescent signal.

A fourth aspect of the invention relates to a method of preparing a reaction mixture for amplifying either or both of HIV-1 M group nucleic acids and HIV-1 O group nucleic acids. The invented method includes steps for: (a) selecting a first amplification primer that includes a sequence that independently hybridizes to a first strand of either HIV-1 M group target nucleic acids or HIV-1 O group target nucleic acids; (b) selecting a second amplification primer that includes a sequence that hybridizes to enzymatic extension products of the first amplification primer using the first strand of either HIV-1 M group target nucleic acids or HIV-1 O group target nucleic acids as a template; (c) selecting a hybridization probe that hybridizes to amplicons synthesized by the use of the first and the second amplification primers, wherein neither the first primer target-hybridizing sequence nor the second primer target-hybridizing sequence is fully complementary to the HIV-1 M group or HIV-1 O group nucleic acids or the complements thereof, and wherein the first amplification primer, the second amplification primer, and the hybridization probe are further selected to amplify in an in vitro amplification reaction HIV-1 M group nucleic acids and HIV-1 O group nucleic acids with substantially equal efficiencies; and (d) combining in a single reaction vessel the first amplification primer, the second amplification primer, and the hybridization probe. In a preferred embodiment, the reaction mixture includes no more than two primers and a single hybridization probe for amplifying and detecting the HIV-1 M group nucleic acids and HIV-1 O group nucleic acids. More preferably, the in vitro amplification reaction is an isothermal in vitro amplification reaction. Still more preferably, the isothermal in vitro amplification reaction is a transcription associated amplification reaction that is either a TMA reaction or a NASBA reaction.

A fifth aspect of the invention relates to a composition for amplifying HIV-1 M group target nucleic acids and HIV-1 O group target nucleic acids. The invented composition includes: (a) a first amplification primer that includes a first primer target-hybridizing sequence that independently hybridizes to a first strand of HIV-1 M group target nucleic acids and to a first strand of HIV-1 O group target nucleic acids; and (b) a second amplification primer that includes a second primer target-hybridizing sequence that hybridizes to enzymatic extension products of the first amplification primer using the first strand of either HIV-1 M group target nucleic acids or HIV-1 O group target nucleic acids as a template. In accordance with this aspect of the invention, neither the first primer target-hybridizing sequence nor the second primer target-hybridizing sequence is fully complementary to the HIV-1 M group or HIV-1 O group target nucleic acids or the complements thereof. In a preferred embodiment, the composition also includes a hybridization probe that hybridizes to an amplification product produced in an in vitro amplification reaction by the combined activity of the first and second amplification primers using as a template either HIV-1 M group target nucleic acids or HIV-1 O group target nucleic acids. More preferably, the composition amplifies HIV-1 M group target nucleic acids and HIV-1 O group target nucleic acids in the in vitro nucleic acid amplification reaction with substantially equal efficiency. Still more preferably, the first primer target-hybridizing sequence consists essentially of SEQ ID NO:15, and the second primer target-hybridizing sequence consists essentially of SEQ ID NO:5. In an alternative preferred embodiment, the hybridization probe is a molecular torch or a molecular beacon. In certain instances, it is preferred for the hybridization probe to be a molecular torch. In other preferred embodiments, the second primer target-hybridizing sequence consists essentially of SEQ ID NO:5. When this is the case, the first primer target-hybridizing sequence may consist essentially of SEQ ID NO:15. In still other preferred embodiments, when the composition includes the above-mentioned hybridization probe, the first primer target-hybridizing sequence may consist essentially of SEQ ID NO:15, and the second primer target-hybridizing sequence may consist essentially of SEQ ID NO:5. More preferably, the hybridization probe is a molecular torch.

A sixth aspect of the invention relates to a reaction mixture for amplifying either HIV-1 M group nucleic acids or HIV-1 O group nucleic acids. The invented reaction mixture includes: (a) a first amplification primer that includes a first primer target-hybridizing sequence that independently hybridizes to a first strand of HIV-1 M group nucleic acids and a first strand of HIV-1 O group nucleic acids; (b) a second amplification primer that includes a second primer target-hybridizing sequence that hybridizes to an enzymatic extension product of the first amplification primer, using as a template either the first strand of HIV-1 M group nucleic acids or the first strand of HIV-1 O group nucleic acids; and (c) a molecular torch hybridization probe that hybridizes to an amplicon synthesized by the combined activity of the first amplification primer and the second amplification primer. In accordance with this aspect of the invention, neither the first primer target-hybridizing sequence nor the second primer target-hybridizing sequence is fully complementary to the HIV-1 M group or HIV-1 O group nucleic acids or the complements thereof. Significantly, the HIV-1 M group nucleic acids and HIV-1 O group nucleic acids amplify in the reaction mixture with substantially equal efficiency.

DEFINITIONS

The following terms have the following meanings for the purpose of this disclosure, unless expressly stated to the contrary herein.

As used herein, a "biological sample" is any tissue or polynucleotide-containing material obtained from a human, animal or environmental sample. Biological samples in accordance with the invention include peripheral blood, plasma, serum or other body fluid, bone marrow or other organ, biopsy tissues or other materials of biological origin. A biological sample may be treated to disrupt tissue or cell structure, thereby releasing intracellular components into a solution which may contain enzymes, buffers, salts, detergents and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. Homogeneous detectable labels are preferred when using labeled probes for detecting HIV-1 nucleic acids. Examples of homogeneous labels have been described in detail by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of hybridized probe from non-hybridized probe prior to determining the extent of specific probe hybridization. Exemplary homogeneous assays, such as those described herein, can employ molecular beacons or other self-reporting probes which emit fluorescent signals when hybridized to an appropriate target, chemiluminescent acridinium ester labels which can be selectively destroyed by chemical means unless present in a hybrid duplex, and other homogeneously detectable labels that will be familiar to those having an ordinary level of skill in the art.

As used herein, "amplification" or "amplifying" refers to an in vitro procedure for obtaining multiple copies of a target nucleic acid sequence, its complement or fragments thereof.

By "target nucleic acid" or "target" is meant a nucleic acid molecule containing a target nucleic acid sequence.

By "target nucleic acid sequence" or "target sequence" or "target region" is meant a specific deoxyribonucleotide or ribonucleotide sequence comprising all or part of the nucleotide sequence of a single-stranded nucleic acid molecule, and possibly comprising (when specified) the deoxyribonucleotide or ribonucleotide sequence complementary thereto. In general, a target nucleic acid sequence that is to be amplified will be positioned between two oppositely disposed primers, and will include the portion of the target nucleic acid molecule that is partially or fully complementary to each of the primers. In the context of the invention, a target nucleic acid molecule may be, for example, an HIV-1 nucleic acid molecule. The portion of this target nucleic acid molecule to be amplified in an in vitro nucleic acid amplification reaction would be referred to as the "target nucleic acid sequence" to be amplified.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al. are preferred for conducting nucleic acid amplification procedures of the type disclosed herein. Another example of a transcription associated amplification method is the Nucleic Acid Sequence-Based Amplification (NASBA) method disclosed in U.S. Pat. No. 5,554,517.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits. Common nucleotide base moieties are guanine (G), adenine (A), cytosine (C), thymine (T) and uracil (U), although other rare or modified nucleotide bases, including nucleotide analogs, able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

As used herein, a "hybridization probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. These non-complementary sequences may comprise a promoter sequence, a restriction endonuclease recognition site, or sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "amplification primer" is an oligonucleotide that hybridizes to a target nucleic acid, or its complement, and participates in a nucleic acid amplification reaction. For example, amplification primers, or more simply "primers," may be optionally modified oligonucleotides which are capable of hybridizing to a template nucleic acid and which have a 3' end that can be extended by a DNA polymerase activity. In general, a primer will have a downstream HIV-1 complementary sequence, and optionally an upstream sequence that is not complementary to HIV-1 nucleic acids. The optional upstream sequence may, for example, serve as an RNA polymerase promoter or contain restriction endonuclease cleavage sites.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0-3 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-3 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are preferably at least about 70%, more preferably at least about 80%, still more preferably at least about 90%, and most preferably about 100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57 particularly at §§ 9.50-9.51, 11.12-11.13, 11.45-11.47 and 11.55-11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target sequence from unbound material in a sample.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

By "RNA and DNA equivalents" or "RNA and DNA equivalent bases" is meant molecules, such as RNA and DNA, having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

As used herein, an "in vitro amplification reaction" is an enzyme-catalyzed reaction that results in the synthesis of multiple copies of a target nucleic acid sequence, its complement or fragments thereof. Examples of some useful amplification methods that can be used for preparing in vitro amplification reactions are given below. An "isothermal in vitro amplification reaction" is an in vitro amplification reaction that can synthesize multiple copies of a target nucleic acid sequence, its complement or fragments thereof at a constant temperature (i.e., without thermal cycling).

As used herein, the term "amplicons" refers to the nucleic acid amplification products of an in vitro amplification reaction. Amplicons may comprise DNA or RNA, depending on the nature of the in vitro amplification reaction used to produce the amplicons.

As used herein, the "target-hybridizing sequence" of a hybridization probe or an amplification primer refers to the base sequence of the probe or primer which participates in a duplex structure upon hybridization to an appropriate target nucleic acid. In the case of a promoter-primer that includes a downstream sequence complementary to the target nucleic acid and an upstream T7 promoter sequence which is not complementary to the target nucleic acid, the non-complementary promoter sequence of the primer would not be considered a target-hybridizing sequence. Conversely, a downstream primer sequence sufficiently complementary to the target nucleic acid to be able to form a duplex structure upon hybridization to the target nucleic acid would be a target-hybridizing sequence. If the target-hybridizing sequence of the primer contains occasional mismatches to the target nucleic acid sequence, then it would not be fully complementary to the target nucleic acid sequence within the target nucleic acid molecule.

By "fully complementary" is meant 100% base complementarity between two polynucleotide molecules over the length of the target-hybridizing sequence.

As used herein, monitoring amplicon production "as a function of time" refers to the process of taking periodic measurements of the amount of amplicon present in an in vitro amplification reaction, and associating that measured amount with the time elapsed since initiating the in vitro amplification reaction. For example, periodic measurements can be taken at the same point of different cycles of an amplification reaction, or at periodic time intervals (such as every 20 seconds) during a reaction that does not involve physical cycling of reaction steps.

As used herein, a "standard curve" is a representation that relates (1) a pre-amplification amount of a polynucleotide, and (2) some time-dependent indicia of a post-amplification amount of a corresponding amplicon. For example, a standard curve can be a graph having known numbers of input template molecules plotted on the x-axis, and a time value required for the amplification reaction to achieve some level of detectable amplicon production plotted on the y-axis. Standard curves typically are produced using control polynucleotide standards containing known numbers of polynucleotide templates. Standard curves can be stored in electronic form or can be represented graphically. The pre-amplification amount of an analyte polynucleotide in a test sample can be determined by comparing a measured time-dependent value obtained for the test sample with a standard curve, as will be familiar to those having an ordinary level of skill in the art.

By an "HIV-1 standard" is meant a known number of copies of an HIV-1 polynucleotide, without specifying the HIV-1 genotype.

By an "HIV-1 M group standard" is meant a known number of copies of an HIV-1 M group polynucleotide.

By an "HIV-1 O group standard" is meant a known number of copies of an HIV-1 O group polynucleotide.

As used herein, the process step of "selecting" an amplification primer or hybridization probe means choosing an amplification primer or hybridization probe having certain specified features.

As used herein, two different nucleic acid targets are said to amplify with "substantially equal efficiency" when the rates of amplicon synthesis are substantially equal in in vitro amplification reactions conducted using similar numbers of the two different nucleic acid targets as templates. Practically speaking, it is not necessary to amplify all species of HIV-1 nucleic acids with identical efficiencies to achieve the benefits of the invention. Instead, it is only necessary to use primers and a probe that will yield substantially equal amplification efficiencies. By this it is meant that, for independent in vitro amplification reactions conducted using HIV-1 M group and O group nucleic acid templates at starting levels of 1,000 copies/reaction, the difference between the average number of starting copies/reaction determined for each target and the actual number of starting copies/reaction is no greater than 1.0 $\log_{10}$ copies/reaction, more preferably no greater than 0.7 $\log_{10}$ copies/reaction, and still more preferably no greater than 0.5 $\log_{10}$ copies/reaction.

As used herein, requiring that two primers and a probe are "selected to amplify in an in vitro amplification reaction HIV-1 M group nucleic acids and HIV-1 O group nucleic acids with substantially equal efficiencies" means that, after screening different combinations of primers and probes, particular combinations are chosen for the characteristic of amplifying HIV-1 M group and HIV-1 O group nucleic acids in in vitro amplification reactions with substantially equal efficiencies.

By "an amplification product produced by the combined activity of said first and second amplification primers using as a template either HIV-1 M group target nucleic acids or HIV-1 O group target nucleic acids" is meant any amplicon synthesized using a combination of two primers, where each of the primers is able to use HIV-1 M group target nucleic acids or HIV-1 O group target nucleic acids, or the complements thereof, as templates.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect HIV-1 nucleic acids in biological samples such as whole blood or plasma. Any component(s), composition(s), or method step(s) that have a material effect on the basic and novel characteristics of the present invention would fall outside of this term.

BRIEF DESCRIPTION OF THE DRAWINGS

FIG. 5A shows results for reactions conducted using a first-strand promoter-primer that included the target-hybridizing sequence of SEQ ID NO:13 and a second-strand primer having the sequence of SEQ ID NO:2. FIG. 5B shows results for reactions conducted using a first-strand promoter-primer that included the target-hybridizing sequence of SEQ ID NO:15 and a second-strand primer having the sequence of SEQ ID NO:2.

FIG. 6A identifies the HIV-1 nucleic acid input into a real-time nucleic acid amplification reaction (x-axis) and the time-of-emergence of the measured fluorescent signal above a background threshold (y-axis). Numerical values shown above each bar indicate the time-of-emergence. FIG. 6B presents the same data shown in FIG. 6A, but plots the average $\log_{10}$ copy number on the y-axis. Numerical values shown above each bar indicate the determined average $\log_{10}$ copy number.

DETAILED DESCRIPTION

Figure 1:
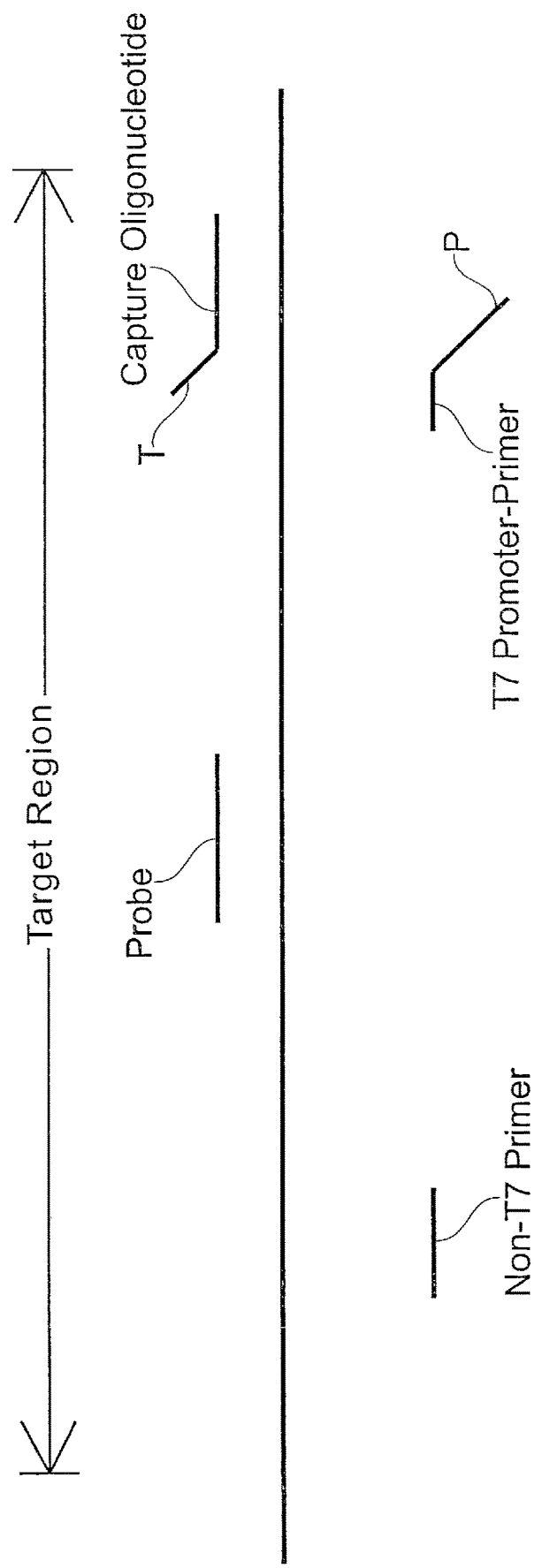
FIG. 1 is a schematic diagram illustrating the various polynucleotides that can be used for detecting a target region within the HIV-1 nucleic acid (represented by a thick horizontal line). Positions of the following nucleic acids are shown relative to the target region: "Capture Oligonucle-otide" refers to the nucleic acid used to hybridize to and capture the target nucleic acid prior to amplification, where "T" refers to a tail sequence used to hybridize an immobilized oligonucleotide having a complementary sequence (not shown); "Non-T7 Primer" and "T7 Promoter-Primer" represent two amplification primers used for conducting TMA, where "P" indicates the promoter sequence of the T7 promoter-primer; and "Probe" refers to the probe used for detecting amplified nucleic acid.

Disclosed herein are compositions, methods and kits for selectively detecting the nucleic acids of HIV-1 in biological samples such as blood, serum, plasma or other body fluid or tissue. The probes, primers and methods of the invention can be used either in diagnostic applications, viral-load testing applications, or for screening donated blood and blood products or other tissues that may contain infectious particles.

Introduction and Overview

The present invention includes compositions (nucleic acid capture oligonucleotides, amplification oligonucleotides and probes), methods and kits that are particularly useful for detecting HIV-1 nucleic acids in a biological sample. To design oligonucleotide sequences appropriate for such uses, known HIV-1 nucleic acid sequences were first compared to identify candidate regions of the viral genome that could serve as reagents in a diagnostic assay. As a result of these comparisons, the capture oligonucleotides, primers and probes shown schematically in FIG. 1 were selected for use in an amplified assay. Portions of sequences containing relatively few variants between the compared sequences were chosen as starting points for designing synthetic oligonucleotides suitable for use in capture, amplification and detection of amplified sequences.

Based on these analyses, the capture oligonucleotide, amplification primer and probe sequences presented below were designed. Those having an ordinary level of skill in the art will appreciate that any primer sequences specific for an HIV-1 target, with or without a T7 promoter sequence, may be used as primers in the various primer-based in vitro amplification methods described below. It is also contemplated that oligonucleotides having the sequences disclosed herein could serve alternative functions in assays for detecting HIV-1 nucleic acids. For example, the capture oligonucleotides disclosed herein could serve as hybridization probes, the hybridization probes disclosed herein could be used as amplification primers, and the amplification primers disclosed herein could be used as hybridization probes in alternative detection assays.

Useful Amplification Methods

Amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. Nos. 5,399,491, 5,554,517, 4,965,188, 5,455,166, and 5,472,840 and Lizardi et al., *BioTechnology* 6:1197 (1988). The disclosures of these documents which describe how to perform nucleic acid amplification reactions are hereby incorporated by reference.

In a highly preferred embodiment of the invention, HIV-1 nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the HIV-1 target RNA at a defined site. Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Structural Features of Primers

As indicated above, a "primer" refers to an optionally modified oligonucleotide which is capable of participating in a nucleic acid amplification reaction. Preferred primers are capable of hybridizing to a template nucleic acid and which has a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3' end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified (e.g., by the addition of propyne groups), as long as the modified base moiety retains the ability to form a non-covalent association with G, A, C, T or U, and as long as an oligonucleotide comprising at least one modified nucleotide base moiety or analog is not sterically prevented from hybridizing with a single-stranded nucleic acid. As indicated below in connection with the chemical composition of useful probes, the nitrogenous bases of primers in accordance with the invention may be conventional bases (A, G, C, T, U), known analogs thereof (e.g., inosine or "I" having hypoxanthine as its base moiety; see *The Biochemistry of the Nucleic Acids* 5-36, Adams et al., ed., 11$^{th}$ ed., 1992), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). Common sugar moieties that comprise the primer backbone include ribose and deoxyribose, although 2'-O-methyl ribose (OMe), halogenated sugars, and other modified sugar moieties may also be used. Usually, the linking group of the primer backbone is a phosphorus-containing moiety, most commonly a phosphodiester linkage, although other linkages, such as, for example, phosphorothioates, methylphosphonates, and non-phosphorus-containing linkages such as peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules, fluorescent moieties (either alone or in combination with "quencher" moieties), and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn, Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). Examples of homogeneously detectable labels include fluorescent labels, electronically detectable labels, and chemiluminescent compounds (e.g., as described by Woodhead et al., in U.S. Pat. No. 5,656,207; by Nelson et al., in U.S. Pat. No. 5,658,737; or by Arnold et al., in U.S. Pat. No. 5,639,604).

In some applications, probes exhibiting at least some degree of self-complementarity are desirable to facilitate detection of probe:target duplexes in a test sample without first requiring the removal of unhybridized probe prior to detection. By way of example, structures referred to as "Molecular Beacons" comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference. Molecular beacons useful for detecting HIV-1 specific nucleic acid sequences may be created by appending to either end of one of the probe sequences disclosed herein, a first nucleic acid arm comprising a fluorophore and a second nucleic acid arm comprising a quencher moiety. In this configuration, the HIV-1 specific probe sequence disclosed herein serves as the target-complementary "loop" portion of the resulting molecular beacon, while the self-complementary "arms" of the probe represent the "stem" portion of the probe.

Another example of a self-complementary hybridization assay probe that may be used in conjunction with the invention is a structure commonly referred to as a "Molecular Torch." These self-reporting probes are designed to include distinct regions of self-complementarity (coined "the target binding domain" and "the target closing domain") which are connected by a joining region and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference.

Molecular torches and molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for the invented molecular torches and molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the BLACK HOLE QUENCHER moieties which are available from Biosearch Technologies, Inc., (Novato, Calif.).

Synthetic techniques and methods of bonding labels to nucleic acids and detecting labels are well known in the art (e.g., see Sambrook et al., *Molecular Cloning, A Laboratory Manual*, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Chemical Composition of Probes

Probes in accordance with the invention comprise polynucleotides or polynucleotide analogs and optionally may carry a detectable label covalently bonded thereto. Nucleosides or nucleoside analogs of the probe comprise nitrogenous heterocyclic bases, or base analogs, where the nucleosides are linked together, for example by phospohdiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Int'l Pub. No. WO 95/32305), phosphorothioate linkages, methylphosphonate linkages or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., N$^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). A probe may comprise only conventional sugars, bases and linkages found in RNA and DNA, or may include both conventional components and substitutions (e.g., conventional bases linked via a methoxy backbone, or a nucleic acid including conventional bases and one or more base analogs).

While oligonucleotide probes of different lengths and base composition may be used for detecting HIV-1 nucleic acids, preferred probes in this invention have lengths of up to 100 nucleotides, and more preferably have lengths of up to 60 nucleotides. Preferred length ranges for the invented oligonucleotides are from 10 to 100 bases in length, or more preferably between 15 and 50 bases in length, or still more preferably between 15 and 30 bases in length. However, the specific probe sequences described below also may be provided in a nucleic acid cloning vector or transcript or other longer nucleic acid and still can be used for detecting HIV-1 nucleic acids.

Selection of Amplification Primers and Detection Probes Specific for HIV-1

Useful guidelines for designing amplification primers and probes with desired characteristics are described herein. The optimal sites for amplifying and probing HIV-1 nucleic acids contain two, and preferably three, conserved regions each greater than about 15 bases in length, within about 200 bases of contiguous sequence. The degree of amplification observed with a set of primers or promoter-primers depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known to those skilled in the art, and are described by Hogan et al., in U.S. Pat. No. 5,840,488, the disclosure of which is hereby incorporated by reference.

The length of the target nucleic acid sequence and, accordingly, the length of the primer sequence or probe sequence can be important. In some cases, there may be several sequences from a particular target region, varying in location and length, which will yield primers or probes having the desired hybridization characteristics. While it is possible for nucleic acids that are not perfectly complementary to hybridize, the longest stretch of perfectly homologous base sequence will normally primarily determine hybrid stability.

Amplification primers and probes should be positioned to minimize the stability of the oligonucleotide:nontarget (i.e., nucleic acid with similar sequence to target nucleic acid) nucleic acid hybrid. It is preferred that the amplification primers and detection probes are able to distinguish between target and non-target sequences. In designing primers and probes, the differences in these Tm values should be as large as possible (e.g., at least 2° C. and preferably 5° C.).

The degree of non-specific extension (primer-dimer or non-target copying) can also affect amplification efficiency. For this reason, primers are selected to have low self- or cross-complementarity, particularly at the 3' ends of the sequence. Long homopolymer tracts and high GC content are avoided to reduce spurious primer extension. Commercially available computer software can aid in this aspect of the design. Available computer programs include MacDNA-SIS™ 2.0 (Hitachi Software Engineering American Ltd.) and OLIGO ver. 6.6 (Molecular Biology Insights; Cascade, Colo.).

Those having an ordinary level of skill in the art will appreciate that hybridization involves the association of two single strands of complementary nucleic acid to form a hydrogen bonded double strand. It is implicit that if one of the two strands is wholly or partially involved in a hybrid, then that strand will be less able to participate in formation of a new hybrid. By designing primers and probes so that substantial portions of the sequences of interest are single stranded, the rate and extent of hybridization may be greatly increased. If the target is an integrated genomic sequence, then it will naturally occur in a double stranded form (as is the case with the product of the polymerase chain reaction). These double-stranded targets are naturally inhibitory to hybridization with a probe and require denaturation prior to the hybridization step.

The rate at which a polynucleotide hybridizes to its target is a measure of the thermal stability of the target secondary structure in the target binding region. The standard measurement of hybridization rate is the $C_0t_{1/2}$ which is measured as moles of nucleotide per liter multiplied by seconds. Thus, it is the concentration of probe multiplied by the time at which 50% of maximal hybridization occurs at that concentration. This value is determined by hybridizing various amounts of polynucleotide to a constant amount of target for a fixed time. The $C_0t_{1/2}$ is found graphically by standard procedures familiar to those having an ordinary level of skill in the art.

Preferred Amplification Primers

Primers useful for conducting amplification reactions can have different lengths to accommodate the presence of extraneous sequences that do not participate in target binding, and that may not substantially affect amplification or detection procedures. For example, promoter-primers useful for performing amplification reactions in accordance with the invention have at least a minimal sequence that hybridizes to the HIV-1 target nucleic acid, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing the desired complementary sequence.

Tables 1 and 2 present specific examples of oligonucleotide sequences that were used as primers for amplifying HIV-1 nucleic acids in the pol region. Table 1 presents the sequences of primers that were complementary to HIV-1 sequences on one strand of nucleic acid. Table 2 presents the sequences of both the HIV-1 target-complementary primers and the full sequences for promoter-primers that were used during development of the invention. Notably, the oligonucleotide sequences in Table 1 and Table 2 are complementary to opposite strands of the HIV-1 nucleic acid.

TABLE 1

Polynucleotide Sequences of Amplification Primers

| Sequence | SEQ ID NO: |
| --- | --- |
| ACAGCAGTACAAATGGCAG | 1 |
| CCACAATTTTAAAAGAAAAGGG | 2 |
| CCACAATTTTAAGAGAAAAGGG | 3 |
| CCACAATTTTAGAAGAAAAGGG | 4 |
| CCACAATTTTGAAAGAAAAGGG | 5 |
| CCACAATTTTAAAGGAAAAGGG | 6 |
| CCACAATTTGAAAAGAAAAGGG | 7 |
| CCACAGTTTTAAAAGAAAAGGG | 8 |
| CCACAATTTTGAAAGAAAAGGGG | 9 |
| CCACAATATTAAAAGAAAAGGG | 10 |
| CCACAATTTTAAAAGAGAAGGGGGGATTGG | 11 |
| CCACAATTTTAAAAGGAAAGGGGGGATTGG | 12 |

Table 2 presents HIV-1 target-complementary oligonucleotide sequences and the corresponding promoter-primer sequences that were used for amplifying HIV-1 nucleic acid sequences in the HIV-1 pol region. As indicated above, promoter-primers that are to be used for practicing the invention include sequences complementary to an HIV-1 target sequence at their 3' ends, and a T7 promoter sequence (presented in lowercase) at their 5' ends.

TABLE 2

Polynucleotide Sequences of Amplification Primers

| Sequence | SEQ ID NO: |
| --- | --- |
| AGTTTGTATGTCTGTTGCTATTATGTCTA | 13 |
| AGTTTGTGTGTCTGTTGCTGTTATGTCTA | 14 |
| AGTTTGTATGTCTGATGCTATTATGTCTA | 15 |
| AGTTTGTATGTCTGGTGCTATTATGTCTA | 16 |
| 5'-aatttaatacgactcactataggggag-AGTTTGTATGTCTGTTGCTATTATGTCTA-3' | 17 |
| 5'-aatttaatacgactcactataggggag-AGTTTGTGTGTCTGTTGCTGTTATGTCTA-3' | 18 |
| 5'-aatttaatacgactcactataggggag-AGTTTGTATGTCTGATGCTATTATGTCTA-3' | 19 |
| 5'-aatttaatacgactcactataggggag-AGTTTGTATGTCTGGTGCTATTATGTCTA-3' | 20 |

Preferred sets of primers for amplifying HIV-1 sequences in the pol region include a first primer that hybridizes an HIV-1 target sequence (such as one of the primers listed in Table 2) and a second primer complementary to the sequence of an extension product of the first primer (such as one of the primer sequences listed in Table 1). In a highly preferred embodiment, the first primer is a promoter-primer that includes a T7 promoter sequence at its 5' end.

Preferred Detection Probes

Another aspect of the invention relates to hybridization probes for detecting HIV-1 nucleic acids. Methods for amplifying a target nucleic acid sequence present in the nucleic acid of HIV-1 can include an optional further step for detecting amplicons. This method includes a step for contacting a test sample with a hybridization assay probe that preferentially hybridizes to the target nucleic acid sequence, or the complement thereof, thereby forming a probe:target duplex that is stable for detection. Next there is a step for determining whether the hybrid is present in the test sample as an indication of the presence or absence of HIV-1 nucleic acids in the test sample. This may involve detecting the probe:target duplex, and preferably involves homogeneous assay systems.

Hybridization assay probes useful for detecting HIV-1 nucleic acid sequences include a sequence of bases substantially complementary to an HIV-1 target nucleic acid sequence. Thus, probes of the invention preferably hybridize one strand of an HIV-1 target nucleic acid sequence, or the complement thereof. These probes may optionally have additional bases outside of the targeted nucleic acid region which may or may not be complementary to the HIV-1 nucleic acid.

Certain highly preferred probes are able to hybridize to HIV-1 target nucleic acids under conditions suitable for performing a nucleic acid amplification reaction, such as those described herein. Examples of particularly preferred probes useful in connection with this aspect of the invention include molecular beacons and molecular torches.

Other preferred probes are sufficiently homologous to the target nucleic acid to hybridize under stringent hybridization conditions corresponding to about 60° C. when the salt concentration is in the range of 0.6-0.9 M. Preferred salts include lithium chloride, but other salts such as sodium chloride and sodium citrate also can be used in the hybridization solution. Example high stringency hybridization conditions are alternatively provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA.

Probes in accordance with the invention have sequences complementary to, or corresponding to a portion of the HIV-1 genome. Certain probes that are preferred for detecting HIV-1 nucleic acid sequences have a probe sequence, which includes the target-complementary sequence of bases together with any base sequences that are not complementary to the nucleic acid that is to be detected, in the length range of from 10-100 nucleotides. Certain specific probes that are preferred for detecting HIV-1 nucleic acid sequences have target-complementary sequences in the length range of from 10-50, from 10-20, or from 10-15 nucleotides. Of course, these target-complementary sequences may be linear sequences, or may be contained in the structure of a molecular beacon, molecular torch or other construct having one or more optional nucleic acid sequences that are non-complementary to the HIV-1 target sequence that is to be detected. As indicated above, probes may be made of DNA, RNA, a combination of DNA and RNA, a nucleic acid analog, or contain one or more modified nucleosides (e.g., a ribonucleoside having a 2'-O-methyl substitution to the ribofuranosyl moiety).

Certain highly preferred probes include a detectable label. In one embodiment, the detectable label is a fluorescent label which may, optionally, be used in combination with a quencher moiety. In other embodiments, the label is an acridinium ester joined to the probe by means of a non-nucleotide linker. For example, detection probes can be labeled with chemiluminescent acridinium ester compounds that are attached via a linker substantially as described in U.S. Pat. No. 5,585,481; and in U.S. Pat. No. 5,639,604, particularly as described at column 10, line 6 to column 11, line 3, and in Example 8. The disclosures contained in these patent documents are hereby incorporated by reference. Of course, highly preferred probes for use in time-dependent amplicon detection include molecular beacons and molecular torches.

Table 3 presents the target-complementary base sequences, and full sequences of some of the hybridization probes that were used for detecting HIV-1 amplicons. Since alternative probes for detecting HIV-1 nucleic acid sequences can hybridize to the opposite-sense strand of HIV-1, the present invention also includes oligonucleotides that are complementary to the sequences presented in the table. The target-hybridizing sequence of SEQ ID NO:21 was incorporated into the molecular beacon having the sequence of SEQ ID NO:22. The target-hybridizing sequence of SEQ ID NO:23 was incorporated into the molecular torch having the sequence of SEQ ID NO:24. Both the molecular beacon and the molecular torch appearing in Table 3 were labeled with a fluorescein moiety at its 5' end, and with a DABCYL quencher moiety at its 3' end.

TABLE 3

Polynucleotide Sequences of HIV-1 Detection Probes

| Sequence | SEQ ID NO: |
|---|---|
| UGGIGGGUACAGUGC | 21 |
| CCGUGGIGGGUACAGUGCCACGG3' | 22 |
| GGIGGGUACAGUGC | 23 |
| CGGIGGGUACAGUGC(C9)CCCCG | 24 |

As indicated above, any number of different backbone structures can be used as a scaffold for the nucleobase sequences of the invented hybridization probes. In certain highly preferred embodiments, the probe sequence used for detecting HIV-1 amplicons includes a methoxy backbone, or at least one methoxy linkage in the nucleic acid backbone.

Selection and Use of Capture Oligonucleotides

Preferred capture oligonucleotides include a first sequence that is complementary to an HIV-1 sequence (i.e., an "HIV-1 target sequence") covalently attached to a second sequence (i.e., a "tail" sequence) that serves as a target for immobilization on a solid support. Any backbone to link the base sequence of a capture oligonucleotide may be used. In certain preferred embodiments the capture oligonucleotide includes at least one methoxy linkage in the backbone. The tail sequence, which is preferably at the 3' end of a capture oligonucleotide, is used to hybridize to a complementary base sequence to provide a means for capturing the hybridized target HIV-1 nucleic acid in preference to other components in the biological sample.

Although any base sequence that hybridizes to a complementary base sequence may be used in the tail sequence, it is preferred that the hybridizing sequence span a length of about 5-50 nucleotide residues. Particularly preferred tail sequences are substantially homopolymeric, containing about 10 to about 40 nucleotide residues, or more preferably about 14 to about 30 residues. A capture oligonucleotide according to the present invention may include a first sequence that specifically binds an HIV-1 target polynucleotide, and a second sequence that specifically binds an oligo(dT) stretch immobilized to a solid support.

Using the components illustrated in FIG. 1, one assay for detecting HIV-1 sequences in a biological sample includes the steps of capturing the target nucleic acid using the capture oligonucleotide, amplifying the captured target region using at least two primers, and detecting the amplified nucleic acid by first hybridizing the labeled probe to a sequence contained in the amplified nucleic acid and then detecting a signal resulting from the bound labeled probe.

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices or particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size ±about 5%).

Retrieving the target nucleic acid:capture oligonucleotide:immobilized probe complex effectively concentrates the target nucleic acid (relative to its concentration in the biological sample) and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Useful capture oligonucleotides may contain mismatches to the above-indicated sequences, as long as the mismatched sequences hybridize to the HIV-1 nucleic acid containing the sequence that is to be amplified. Each capture oligonucleotide described herein included one of the HIV-1 sequences presented in Table 4 linked to a poly-(dA) tail at its 3' end. All of the capture oligonucleotides also included three optional thymidine nucleotides interposed between the HIV-1 complementary sequence and the poly-(dA) tail. The presence of these thymidine nucleotides is not believed to be essential for success of the capture procedure. The three thymidine nucleotides and the poly-(dA) tail were synthesized using DNA precursors, while the HIV-1 complementary portions of the oligonucleotides were synthesized using 2'-OMe nucleotide analogs.

TABLE 4

HIV-1 Complementary Portions of Capture Oligonucleotides

| Sequence | SEQ ID NO: |
| --- | --- |
| GCUGGAAUAACUUCUGCUUCUAU | 25 |
| GCUGGAAUAGCUUCUGCUUCUAU | 26 |
| UCUGCUGUCCCUGUAAUAAACCCG | 27 |
| UCUGCUGUCCCUGUGAUAAACCCG | 28 |

Preferred Methods for Amplifying and Detecting HIV-1 Polynucleotide Sequences

Preferred methods of the present invention are described and illustrated by the Examples presented below. FIG. 1 schematically illustrates one system that may be used for detecting a target region of the HIV-1 genome (shown by a thick solid horizontal line). This system includes four oligonucleotides (shown by the shorter solid lines): one capture oligonucleotide that includes a sequence that hybridizes specifically to an HIV-1 sequence in the target region and a tail ("T") that hybridizes to a complementary sequence immobilized on a solid support to capture the target region present in a biological sample; one T7 promoter-primer which includes a sequence that hybridizes specifically to an HIV-1 sequence in the target region and a T7 promoter sequence ("P") which, when double-stranded, serves as a functional promoter for T7 RNA polymerase; one non-T7 primer which includes a sequence that hybridizes specifically to a first strand cDNA made from the target region sequence using the T7 promoter-primer; and one labeled probe which includes a sequence that hybridizes specifically to a portion of the target region that is amplified using the two primers.

As indicated above, amplifying the captured target region using the two primers can be accomplished by any of a variety of known nucleic acid amplification reactions that will be familiar to those having an ordinary level of skill in the art. In a preferred embodiment, a transcription-associated amplification reaction, such as TMA, is employed. In such an embodiment, many strands of nucleic acid are produced from a single copy of target nucleic acid, thus permitting detection of the target by detecting probes that are bound to the amplified sequences. Preferably, transcription-associated amplification uses two types of primers (one being referred to as a promoter-primer because it contains a promoter sequence, labeled "P" in FIG. 1, for an RNA polymerase) two enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template.

Referring to FIG. 1, during transcription-mediated amplification, the captured target nucleic acid is hybridized to a first primer shown as a T7 promoter-primer. Using reverse transcriptase, a complementary DNA strand is synthesized from the T7 promoter-primer using the target DNA as a template. A second primer, shown as a non-T7 primer, hybridizes to the newly synthesized DNA strand and is extended by the action of a reverse transcriptase to form a DNA duplex, thereby forming a double-stranded T7 promoter region. T7 RNA polymerase then generates multiple RNA transcripts by using this functional T7 promoter. The autocatalytic mechanism of TMA employs repetitive hybridization and polymerization steps following a cDNA synthesis step using the RNA transcripts as templates to produce additional transcripts, thereby amplifying target region-specific nucleic acid sequences.

The detecting step uses at least one detection probe that binds specifically to the amplified RNA transcripts or amplicons described above. Preferably, the detection probe is labeled with a label that can be detected using a homogeneous detection system. For example, the labeled probe can be labeled with an acridinium ester compound from which a chemiluminescent signal may be produced and detected, as described above. Alternatively, the labeled probe may comprise a fluorophore or a combination of fluorophore and quencher moieties. Molecular beacons and molecular torches are alternative embodiments of such labeled probes that may be used in homogeneous detection systems.

Use of a Standard Curve—Quantifying Pre-Amplification Amounts of Analyte Polynucleotide In general, the invented methods can involve the step of consulting a standard curve that relates pre-amplification amounts of analyte polynucleotide and post-amplification amounts of analyte amplicon.

Since real-time amplification reactions advantageously feature quantitative relationships between the number of analyte polynucleotides input into the reaction and the number of analyte amplicons synthesized as a function of time, the number of analyte polynucleotides present in a test sample can be determined using a standard curve. For example, a plurality of amplification reactions containing known amounts of a polynucleotide standard can be run in parallel with an amplification reaction prepared using a test sample containing an unknown number of analyte polynucleotides. Alternatively, a standard curve can be prepared in advance so that it is unnecessary to prepare a curve each time an analytical procedure is carried out. Such a curve prepared in advance can even be stored electronically in a memory device of a testing instrument. A standard curve having pre-amplification amounts of the polynucleotide standard on a first axis and some indicia of the time required to effect a certain level of nucleic acid amplification (such as a time-of-emergence above a background signal) on a second axis is then prepared. The post-amplification amount of analyte amplicon measured for the test reaction is then located on the post-amplification axis of the standard curve. The corresponding value on the other axis of the curve represents the pre-amplification amount of analyte polynucleotide that was present in the test reaction. Thus, determining the number of molecules of analyte polynucleotide present in the test sample is accomplished by consulting the standard curve, or more particularly by comparing the quantitative results obtained for the test sample with the standard curve, a procedure that will be familiar to those having an ordinary level of skill in the art.

The procedures described herein can easily be used to quantify analyte polynucleotides present in a test sample. Indeed, if a plurality of standard control amplification reactions are initiated using known numbers of an analyte polynucleotide standard, and if a test reaction that includes an unknown number of analyte polynucleotide molecules is carried out, then it becomes possible after measuring the time required to effect a certain level of amplification in each reaction to determine the number of analyte polynucleotide molecules that must have been present in the test sample. The relationship between the number of analyte polynucleotide molecules input into standard amplification reaction and the time required to effect a certain level of amplification is conveniently established using a graph. Determining the number of analyte polynucleotide molecules present in a test sample is simply a matter of determining from the standard graph the number of analyte polynucleotide molecules that correspond to a measured analyte amplicon signal strength. This illustrates how analyte polynucleotide standards can be used in connection with polynucleotide amplification reactions to quantify pre-amplification amounts of analyte polynucleotide contained in test samples.

Kits for Detecting HIV-1 Nucleic Acids

The present invention also embraces kits for performing polynucleotide amplification reactions using viral nucleic acid templates. Certain preferred kits will contain a hybridization assay probe that includes a target-complementary sequence of bases, and optionally primers or other ancillary oligonucleotides for amplifying the target that is to be detected. Other preferred kits will contain a pair of oligonucleotide primers that may be used for amplifying target nucleic acids in an in vitro amplification reaction. Exemplary kits include first and second amplification oligonucleotides that are complementary to opposite strands of an HIV-1 nucleic acid sequence that is to be amplified. The kits may further contain one or more oligonucleotide detection probes. Still other kits in accordance with the invention may additionally include capture oligonucleotides for purifying HIV-1 template nucleic acids away from other species prior to amplification.

The general principles of the present invention may be more fully appreciated by reference to the following non-limiting Examples. These Examples describe the development of quantitative nucleic acid amplification assays characterized by substantially linear relationships between the time required to yield a positive amplification signal and the initial amount of HIV-1 template nucleic acid included in the reaction. The invented assays are further characterized by high levels of precision in the quantitation of HIV-1 targets at low copy numbers, and by accurate detection of different HIV-1 subtypes, including M group and O group variants.

Oligonucleotide primers disclosed in published international application WO 2003106714, together with a molecular beacon, served as a starting point for the development of the invented assay. As indicated by the evidence presented in Example 1, modifying the initial primer set by substituting one of the primers dramatically improved the quantitative capacity of the assay by increasing the detectability of low levels of the HIV-1 template. In all cases, positive amplification was indicated by the time-dependent appearance of a fluorescent signal in homogeneous assays.

Analysis of the experimental data was performed using a computer-implemented algorithm to establish a substantially linear relationship between the number of HIV-1 template copies included in an amplification reaction and the time at which the fluorescent signal exceeded a background value (i.e., "time-of-emergence" above background). Essentially identical analyses were conducted for all of the time-dependent assays disclosed herein.

As confirmed by the results presented below, similar procedures can be used for quantifying analyte target amounts present in a test sample. More specifically, when known amounts of an analyte polynucleotide are used as calibration standards, it is possible to determine the amount of analyte present in a test sample by comparing the time-dependent appearance of a fluorescent signal measured for the test sample with a standard curve.

Example 1 describes procedures wherein a molecular beacon probe labeled with an interactive fluorophore/quencher pair was used for monitoring time-dependent amplicon production in nucleic acid amplification reactions. Although the molecular beacons described in this Example hybridized to only one strand of the amplified nucleic acid product, probe sequences complementary to the HIV-1 nucleic acid on the opposite strand also fall within the scope of the invention. Results from these procedures indicated that the choice of oligonucleotide primers profoundly affected the quantitative capacity of the assay.

EXAMPLE 1

Time-Dependent Monitoring of HIV-1 M Group, Subtype B Amplicon Production

An in vitro synthesized transcript of known concentration included the sequence

```
                                          (SEQ ID NO: 29)
GGTACCAGCACACAAAGGAATTGGAGGAAATGAACAAGTAGATAAATTA

GTCAGTGCTGGAATCAGGAAAGTACTATTTTTAGATGGAATAGATAAGG

CCCAAGATGAACATGAGAAATATCACAGTAATTGGAGAGCAATGGCTAG

TGATTTTAACCTGCCACCTGTAGTAGCAAAAGAAATAGTAGCCAGCTGT

GATAAATGTCAGCTAAAAGGAGAAGCCATGCATGGACAAGTAGACTGTA

GTCCAGGAATATGGCAACTAGATTGTACACATTTAGAAGGAAAAGTTAT

CCTGGTAGCAGTTCATGTAGCCAGTGGATATATAGAAGCAGAAGTTATT

CCAGCAGAAACAGGGCAGGAAACAGCATATTTTCTTTTAAAATTAGCAG

GAAGATGGCCAGTAAAAACAATACATACTGACAATGGCAGCAATTTCAC

CGGTGCTACGGTTAGGGCCGCCTGTTGGTGGGCGGGAATCAAGCAGGAA
```

-continued
```
TTTGGAATTCCCTACAATCCCCAAAGTCAAGGAGTAGTAGAATCTATGA

ATAAAGAATTAAAGAAAATTATAGGACAGGTAAGAGATCAGGCTGAACA

TCTTAAGACAGCAGTACAAATGGCAGTATTCATCCACAATTTTAAAAGA

AAAGGGGGATTGGGGGGTACAGTGCAGGGGAAAGAATAGTAGACATAA

TAGCAACAGACATACAAACTAAAGAATTACAAAAACAAATTACAAAAAT

TCAAAATTTTCGGGTTTATTACAGGGACAGCAGAAATCCACTTTGGAAA

GGACCAGCAAAGCTCCTCTGGAAAGGTGAAGGGGCAGTAGTAATACAAG

ATAATAGTGACATAAAAGTAGTGCCAAGAAGAAAAGCAAAGATCATTAG

GGATTATGGAAAACAGATGGCAGGTGATGATTGTGTGGCAAGTAGACAG

GATGAGGAT,
``` and served as the source of HIV-1 subtype B template sequences in amplification reactions that employed paired sets of primers. This in vitro transcript contained portions of the HIV-1 genome that included sequences substantially corresponding to, or substantially complementary to, each of the primers used in the procedure. Nucleic acid amplification reactions were performed using a TMA protocol, and were carried out essentially as described by Kacian et al., in U.S. Pat. No. 5,399,491, the disclosure of this U.S. patent having been incorporated by reference hereinabove. Promoter-primers used in the TMA reactions included a T7 promoter sequence AATTTAATACGACTCAC-TATAGGGAG (SEQ ID NO:30) appended upstream of an HIV-1 complementary sequence. The sequence of the T7 promoter is absent from the HIV-1 analyte polynucleotide, and so was not complementary to the HIV-1 template. Amplification reactions were conducted using variable amounts of the HIV-1 in vitro transcript, and about 0.07-0.12 pmoles/µl of each primer in 30 µl reaction volumes.

A molecular beacon capable of hybridizing to the HIV-1 amplicons was synthesized by standard solid-phase phosphite triester chemistry using 3' quencher-linked controlled pore glass (CPG) and 5' fluorophore-labeled phosphoramidite on a Perkin-Elmer (Foster City, Calif.) EXPEDITE model 8909 automated synthesizer. Fluorescein was used as the fluorophore, DABCYL was used as the quencher, and 2'-methoxy nucleotide analogs were used for construction of the molecular beacon. The CPG and phosphoramidite reagents were purchased from Glen Research Corporation (Sterling, Va.). Following synthesis, deprotection and cleavage from the solid support matrix, the probes were purified using polyacrylamide gel electrophoresis followed by HPLC using standard procedures that will be familiar to those having an ordinary level of skill in the art. The target-complementary sequence contained in the molecular beacon, allowing for the substitution of a single inosine nucleotide analog at position four, and the substitution of uricil for thymine bases, was TGGGGGGTACAGTGC (SEQ ID NO:31). Notably, the target-hybridizing sequences of the molecular beacon and molecular torch hybridization probes described herein were not fully complementary to the HIV-1 O group nucleic acids, or HIV-1 O group amplicons synthesized using the primers disclosed herein. Additionally, the target-hybridizing sequences of these probes were not fully complementary to the nucleic acids or amplicons for HIV-1 M group members represented by subtypes A, E and F. Conversely, these target-hybridizing sequences were fully complementary to HIV-1 subtype B amplicons. The overall sequence of the molecular beacon probe used in the procedure was given by SEQ ID NO:22.

Individual wells in a multiwell plate each contained 30 μl of a Tris-buffered solution that included potassium and magnesium salts, N-Acetyl-L-Cysteine, ribonucleotide triphosphates, nucleotide triphosphates and other reagents, a target polynucleotide, and a molecular beacon. The target polynucleotide was included in amounts ranging from 5 to $5 \times 10^6$ copies/reaction. The first-strand promoter-primer for amplifying the HIV-1 template had the target-hybridizing sequence of SEQ ID NO:13 (which was contained within the sequence of SEQ ID NO:17). Second-strand primers had the sequence of either SEQ ID NO:1 or SEQ ID NO:2. Samples were incubated for 10 minutes at 60° C. to facilitate primer annealing, and then incubated at 42° C. for at least 5 minutes. Aliquots of an enzyme reagent that included both MMLV reverse transcriptase and T7 RNA polymerase enzymes were added to each of the tubes using a repeat pipettor. Amplification reactions were carried out at 42° C., and fluorescence readings were taken every 19.4 seconds using a CHROMO4 REAL-TIME DETECTOR (MJ Research; Reno, Nev.), or every 30 seconds using an OPTICON 2 (MJ Research; Reno, Nev.) real-time instrument essentially according to the manufacturer's instructions. Reactions were performed in replicates of 4-8.

Figure 2:
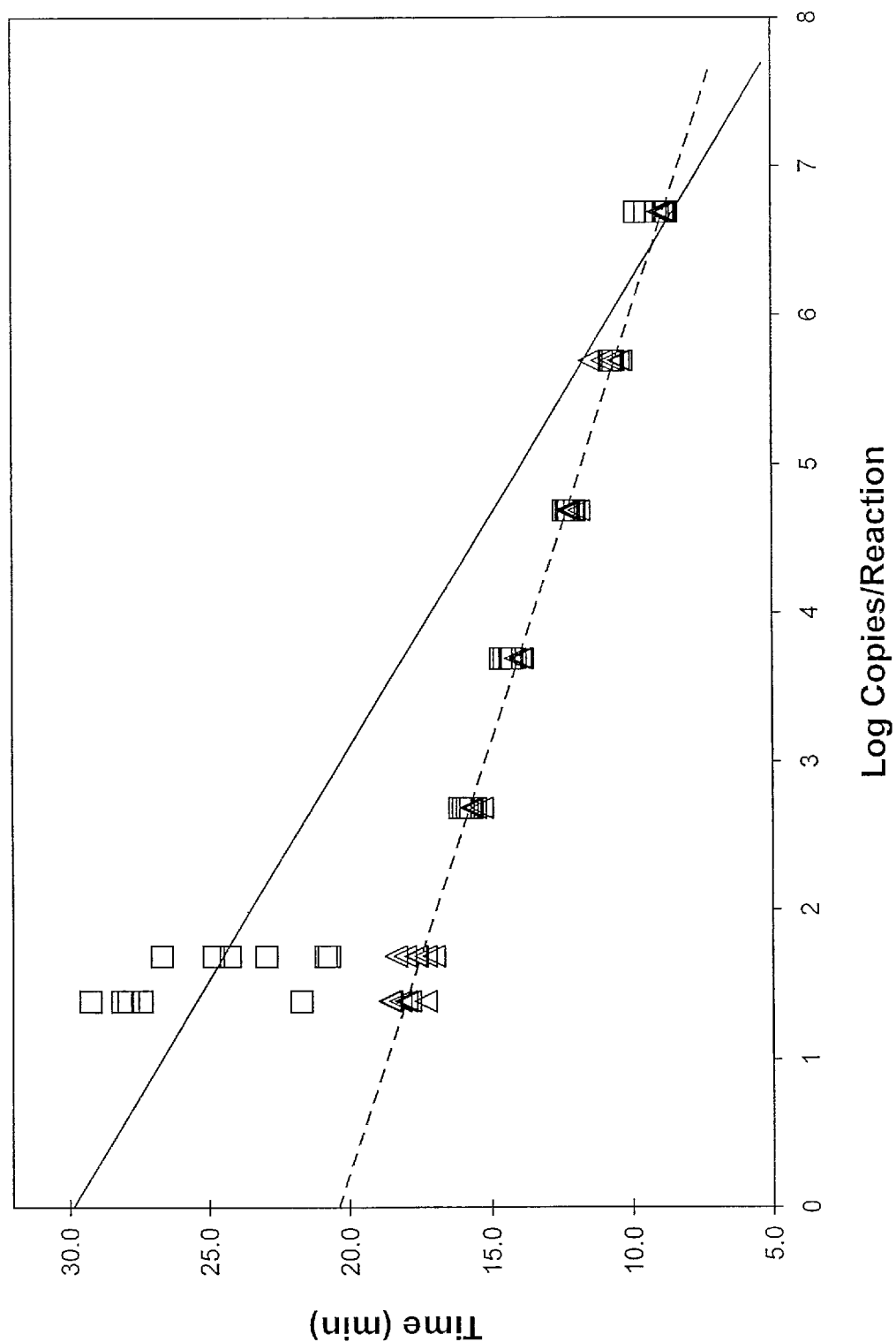
FIG. 2 is a line graph relating the amount of HIV-1 standard input into a real-time nucleic acid amplification reaction (x-axis) and the time-of-emergence of the measured fluorescent signal above a background threshold (y-axis). Results are shown for trials conducted using the primer of SEQ ID NO:1 in combination with a promoter-primer having the target-hybridizing sequence of SEQ ID NO:13 (open squares/solid line), and using the primer of SEQ ID NO:2 in combination with a promoter-primer having the target-hybridizing sequence of SEQ ID NO:13 (open triangles/dashed line).

The results presented in FIG. 2 showed how the substitution of one amplification primer for another dramatically increased the quantitative capacity and precision of the assay. Time-dependent amplification signals obtained using a first-strand promoter-primer that included the target-hybridizing sequence of SEQ ID NO:13 and a second-strand primer having the target-complementary sequence SEQ ID NO:1 showed reduced precision, as judged by the increased spread among individual data points, and substantial divergence from linearity when the level of template used in the reaction fell below 500 copies. This primer combination was preferred for assays intended to quantify HIV-1 nucleic acids at levels greater than 500 copies/reaction. Conversely, time-dependent amplification signals obtained using a first-strand primer that included the target-complementary sequence SEQ ID NO:13 and a second-strand primer having the target-complementary sequence of SEQ ID NO:2 showed improved precision and excellent linearity over the range of from 25 to $5 \times 10^6$ copies/reaction of the nucleic acid template. This latter primer combination advantageously enhanced the low-end quantitative capacity of the assay by 20 fold, a dramatic result that could not have been predicted in advance of this showing.

Although not illustrated in FIG. 2, there was a failure to amplify when using a first-strand promoter-primer having the target-complementary sequence SEQ ID NO:13 and a second-strand primer having the target-complementary sequence SEQ ID NO:1 when using the HIV-1 O group template at levels less than or equal to 50,000 copies/reaction. This demonstrated that the observed loss of precision at low levels of input template was a characteristic of the primer combination, and was independent of the template being amplified. Conversely, the results presented in the following Example confirmed that the combination of a first-strand promoter-primer having the target-hybridizing sequence of SEQ ID NO:13 and a second-strand primer having the sequence of SEQ ID NO:2 advantageously gave linear relationships between input template amounts and the time-dependent amplification signals over an extended range with good precision for templates representing multiple HIV-1 subtypes.

Example 2 demonstrates that HIV-1 M group, subtype B and HIV-1 O group templates could amplify with good precision over an input template range that extended from 25 to $5 \times 10^5$ copies/reaction. Notably, the two templates amplified with somewhat different kinetics.

EXAMPLE 2

Different Kinetic Profiles Characterize Amplification of HIV-1 Variants

Amplification reactions were performed essentially as described under Example 1 with the following modifications. Parallel reactions were conducted using a first-strand promoter-primer having the target-hybridizing sequence of SEQ ID NO:13, a second-strand primer having the target-complementary sequence of SEQ ID NO:2, and variable amounts of either the subtype B template described in Example 1, or an O group template that included the sequence (SEQ ID NO: 32)
AGTGGGTTCATAGAAGCAGAAGTGATACCAGCAGAAACAGGACAAGAAA

CTGCCTACTTCCTGTTAAAACTGGCTGCAAGATGGCCTGTTAAAGTAAT

ACATACAGACAACGGGCCTAATTTTACAAGTACAACTATGAAGGCTGCA

TGTTGGTGGGCCAACATACAACATGAGTTTGGAATACCATATAATCCAC

AAAGTCAAGGAGTAGTAGAAGCCATGAATAAGGAATTAAAATCAATTAT

ACAGCAGGTGAGGGACCAAGCAGAACACTTAAGAACAGCAGTACAAATG

GCAGTATTTGTTCACAATTTTAAAAGAAAAGGGGGATTGGGGGTACA

CTGCAGGAGAAAGGATAATAGACATATTAGCATCACAAATACAAACAAC

AGAATTACAAAAACAAATTTTAAAANTTCACAAATTTCGGGTCTATTAC

AGAGACAGCAGAGACCCTAT.

Like the subtype B template, the O group template was also an in vitro transcript prepared using materials and procedures that will be familiar to those having an ordinary level of skill in the art. Templates were included in the reactions in amounts ranging from 50 to $5 \times 10^5$ copies/reaction.

Figure 3:
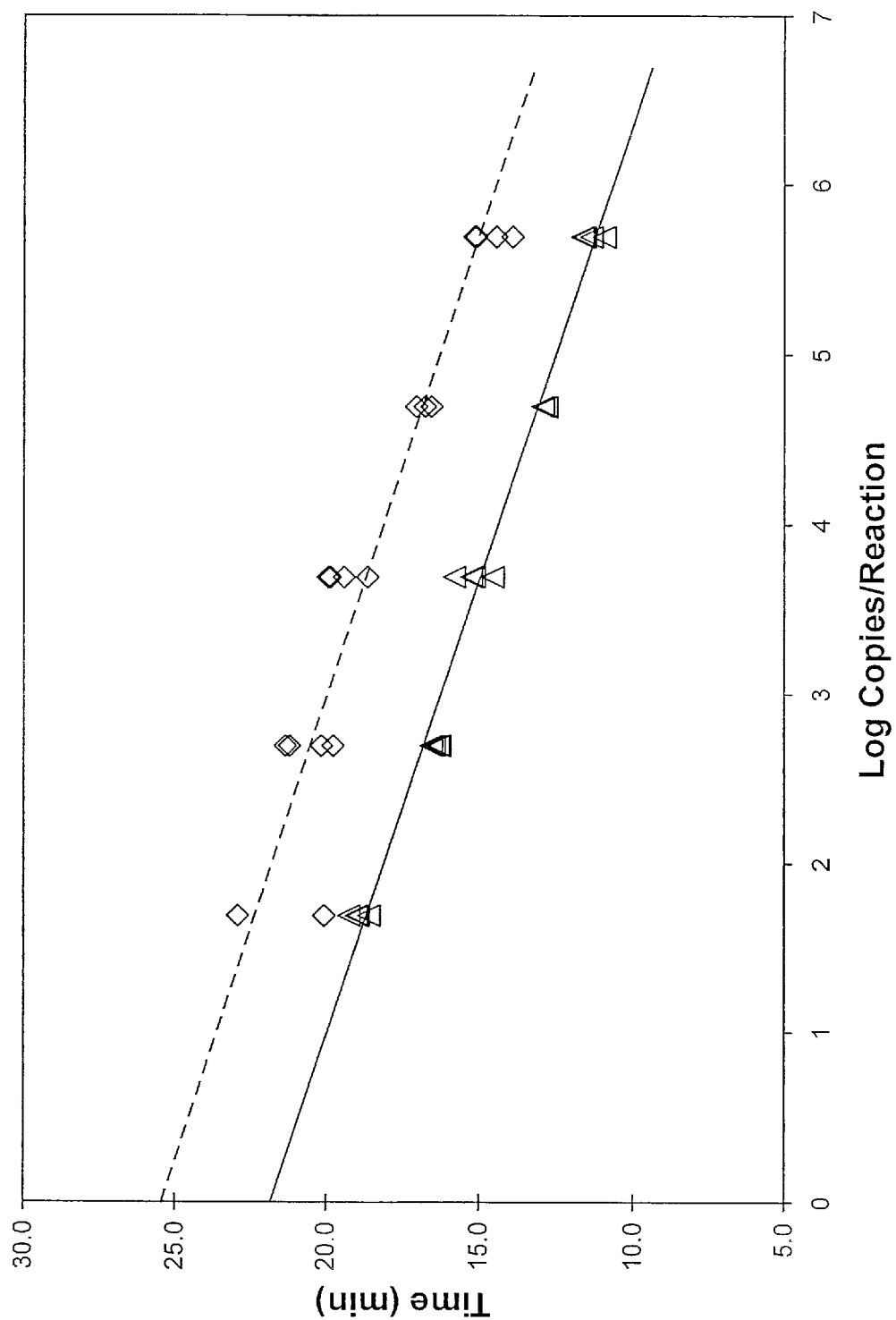
FIG. 3 is a line graph relating the amount of HIV-1 standard input into a real-time nucleic acid amplification reaction (x-axis) and the time-of-emergence of the measured fluorescent signal above a background threshold (y-axis). Results represent time-dependent amplification of HIV-1 subtype B (open triangles/solid line) and HIV-1 O group (open diamonds/dashed line) templates using a first-strand promoter-primer that included the target-hybridizing sequence of SEQ ID NO:13 and a second-strand primer having the sequence of SEQ ID NO:2.

The results presented in FIG. 3 confirmed that advantages associated with the combination of a first-strand primer that included the target-hybridizing sequence of SEQ ID NO:13 and a second-strand primer having the target-complementary sequence of SEQ ID NO:2 extended to amplification of HIV-1 O group templates. More specifically, reactions conducted using this primer combination advantageously exhibited good precision among data points at low levels of HIV-1 template, and linearity of the time-dependent amplification signal. Moreover, the beneficial characteristics of this primer combination were observed for both HIV-1 subtype B and O group templates. As indicated above, tests conducted using the HIV-1 O group template, a first-strand promoter-primer having the target-hybridizing sequence SEQ ID NO:13 and a second-strand primer having the target-complementary sequence SEQ ID NO:1 failed to yield useful amplification signals when the number of input copies of template was below 50,000 copies.

Interestingly, the different HIV-1 template species used in the procedure gave rise to substantially parallel lines on the graph shown in FIG. 3, with the HIV-1 O group template yielding somewhat slower amplification kinetics. For example, a reaction conducted using 5,000 copies of the HIV-1 subtype B template required about 15 minutes to achieve a positive result, but a similar reaction conducted using the HIV-1 O group template required an additional four minutes to achieve the same result. In a quantitative assay that measures the time to achieve a positive result, such a difference conceivably could compromise interpretation of the results and lead to an erroneous conclusion.

Despite the benefits of the primer combination used in this Example, the results indicated that different HIV-1 variants amplified with different kinetic profiles. In the instance illustrated in FIG. 3, detection of a positive amplification signal at 15 minutes would ambiguously indicate the presence of 5,000 copies of the subtype B template, or 500,000 copies of the O group template. A desire to perform assays using a single calibrator, or set of calibrators for quantifying multiple HIV-1 species in a single reaction rendered preferable a close relationship between the amplification profiles of the HIV-1 variants to be detected. Thus, to improve the quantitative capacity of the assay even further, reaction conditions were sought to normalize amplification kinetics for different HIV-1 subtypes.

The following Example discloses amplification primers containing mismatches to both HIV-1 subtype B and HIV-1 O group templates, and use of these primers to normalize the amplification kinetics of HIV-1 variants. The approach used in this procedure was to substitute nucleotides within the sequence of the first-strand primer such that the substitution was complementary to a position contained in the 0 group template, yet non-complementary to the sequence contained in the subtype B template. The object of this approach was to enhance the amplification kinetics of the O group template relative to the subtype B template.

Example 3 describes methods that identified a first-strand primer which enhanced amplification kinetics of HIV-1 O group templates. Contrary to what might have been expected, there was substantially no effect on the amplification kinetics for the HIV-1 subtype B template.

EXAMPLE 3

Enhancement of Amplification Kinetics of HIV-1 O Group Templates

Parallel sets of amplification reactions were prepared to compare the effects of two different primer combinations on the kinetics of amplification of HIV-1 subtype B and HIV-1 O group templates. In each instance, a first-strand promoter-primer having the target-hybridizing sequence of SEQ ID NO:13 or SEQ ID NO:15 was used in combination with a second-strand primer having the target-complementary sequence of SEQ ID NO:2. Notably, the sequence of SEQ ID NO:15 differed from the sequence of SEQ ID NO:13 by the substitution of adenine for thymidine at position 15 in the target-hybridizing portion of the primer. This substitution corresponds to position 41 of the promoter-primers identified by SEQ ID NO:19 and SEQ ID NO:17. Amounts of HIV-1 templates used in the reactions ranged from 5 to $5 \times 10^4$ copies/reaction. Amplification reactions were prepared and monitored using materials and procedures essentially as described above.

Figure 4A:
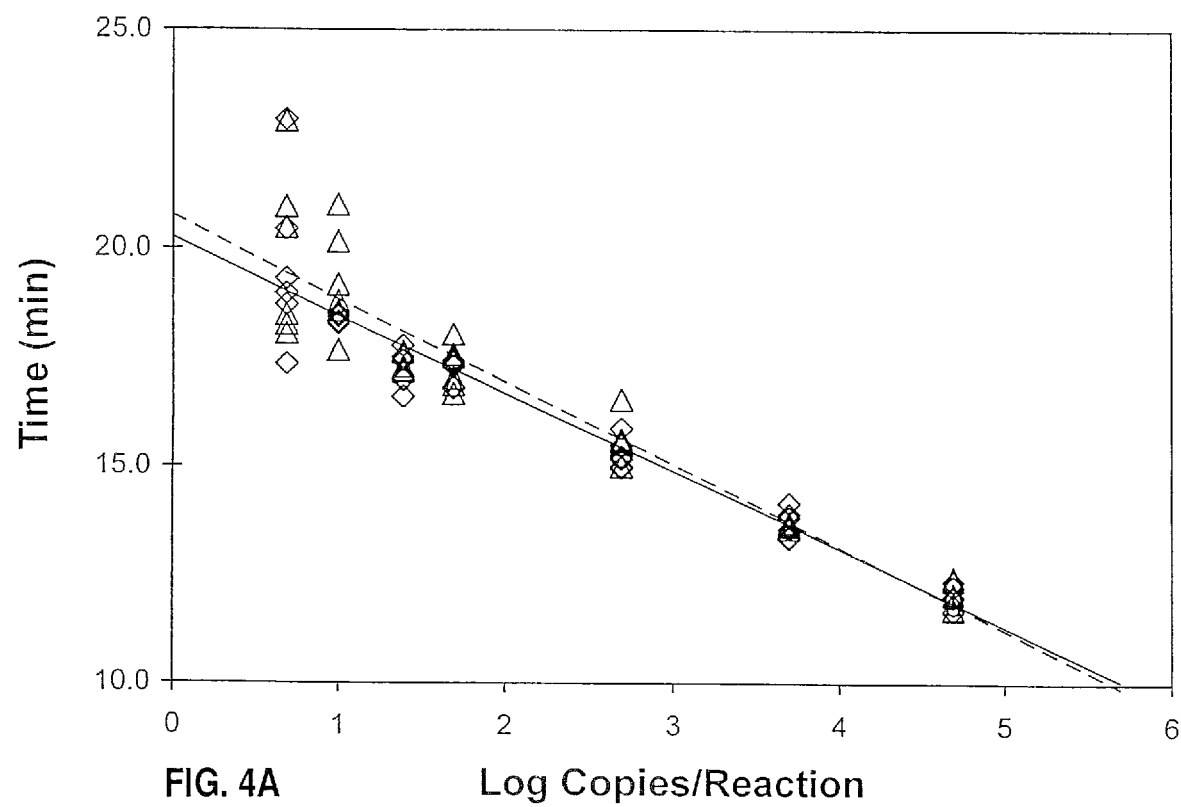
FIGS. 4A-4B are line graphs relating the amount of HIV-1 standard input into a real-time nucleic acid amplification reaction (x-axis) and the time-of-emergence of the measured fluorescent signal above a background threshold (y-axis). Results represent time-dependent amplification of HIV-1 subtype B (FIG. 4A) and HIV-1 O group (FIG. 4B) templates using a first-strand promoter-primer that included the target-hybridizing sequence of SEQ ID NO:13 and a second-strand primer having the sequence of SEQ ID NO:2 (open triangles/dashed lines), or a first-strand promoter-primer that included the target-hybridizing sequence of SEQ ID NO:15 and a second-strand primer having the sequence of SEQ ID NO:2 (open diamonds/solid lines).
Figure 4B:
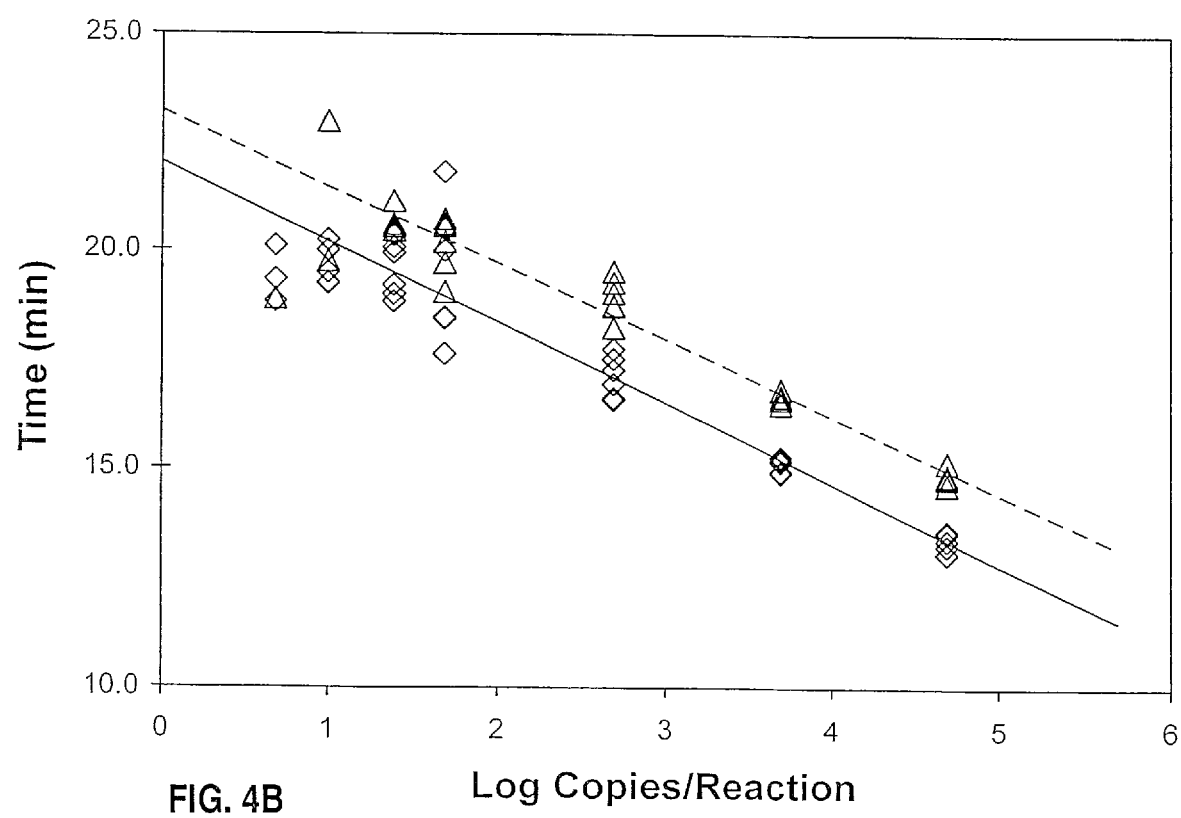

The results presented in FIGS. 4A-4B indicated that substitution of the primer having the target-hybridizing sequence of SEQ ID NO:15 for the primer having the target-hybridizing sequence of SEQ ID NO:13 had different effects on the amplification kinetics of the different templates. More specifically, FIG. 4A shows that the different primer sets amplified the HIV-1 subtype B template with substantially identical kinetics. However, FIG. 4B shows that the HIV-1 O group template amplified with somewhat more rapid kinetics over the full range of input template values tested when using the primer having the target-hybridizing sequence of SEQ ID NO:15 instead of SEQ ID NO:13. Accordingly, the combination of primers that included the target-hybridizing sequences SEQ ID NO:15 and SEQ ID NO:2 advantageously amplified the different HIV-1 template species with kinetics that more closely approximated each other when compared with the combination of primers that included the target-hybridizing sequences SEQ ID NO:13 and SEQ ID NO:2.

In a related procedure, the different primer combinations were used to amplify independent templates representing HIV-1 subtypes A-C, E-F, G/A, H and the HIV-1 O group. The time required to yield a positive amplification signal was determined for input levels of template equaling 1,000 copies/reaction. Reactions were performed using replicates of six.

Figure 5A:
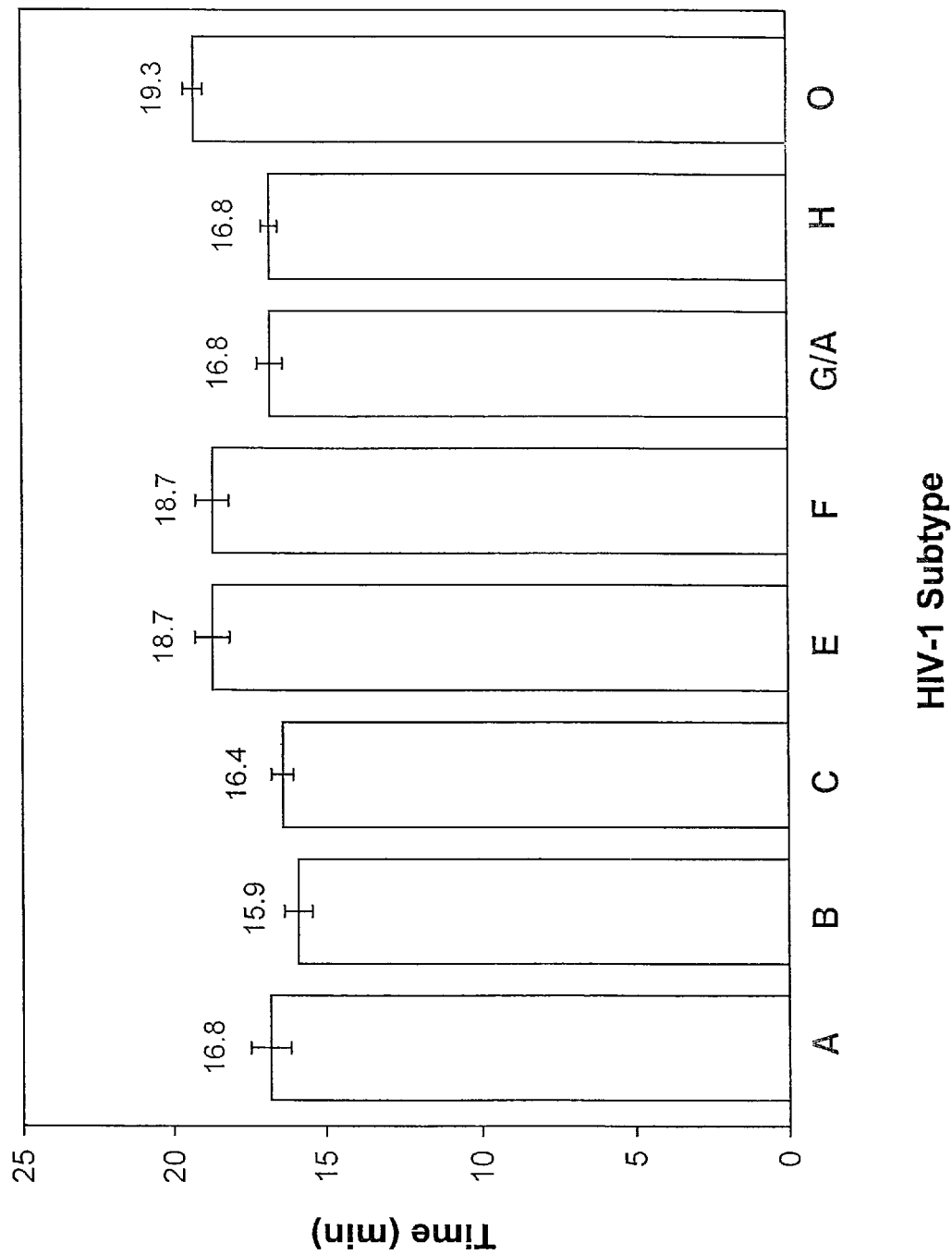
FIGS. 5A-5B are bar graphs representing the time-of-emergence of measured fluorescent signals above a background threshold (y-axis) for different HIV-1 variants at 1,000 copies/reaction.
Figure 5B:
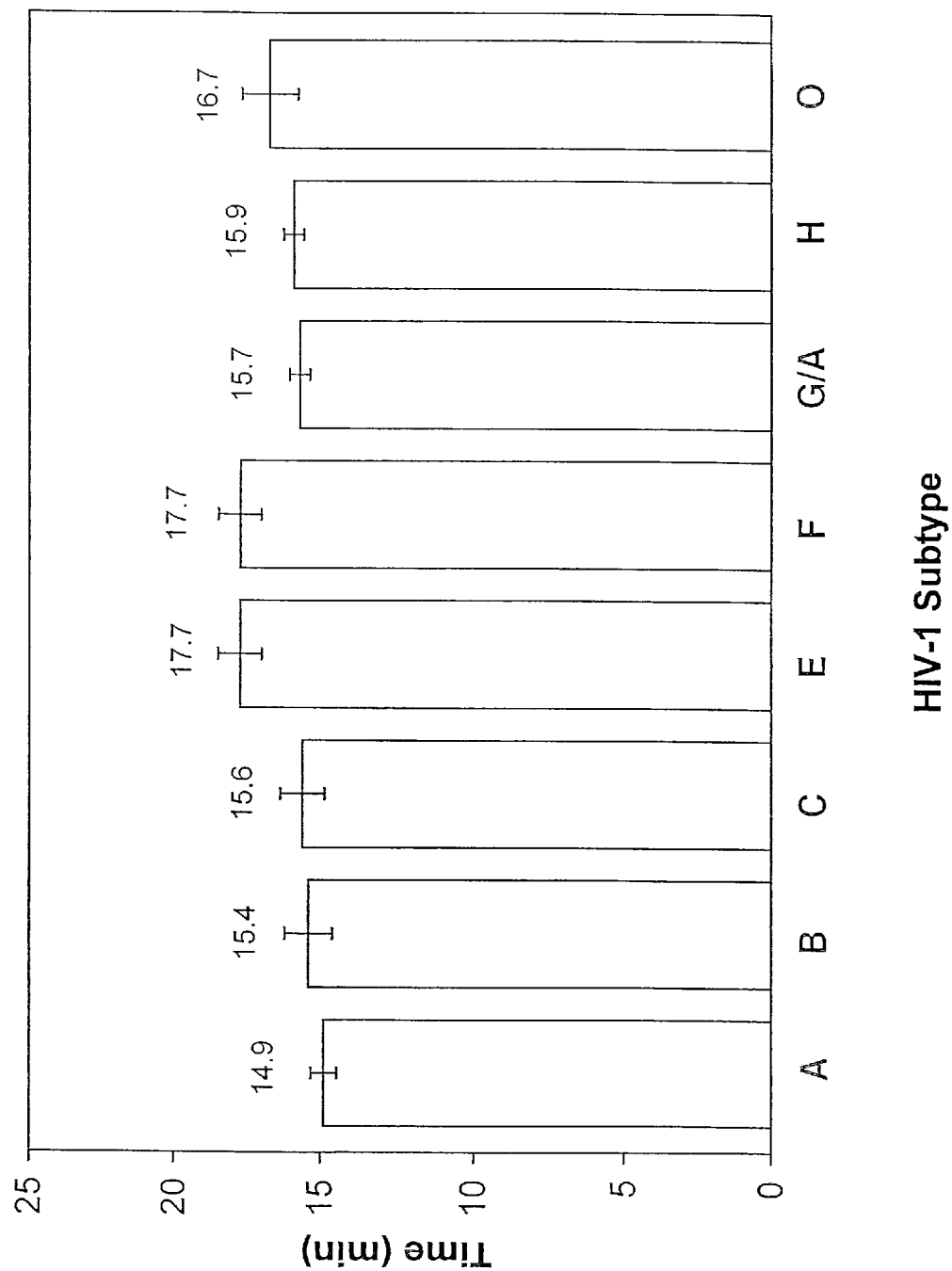

The bar graphs in FIGS. 5A-5B demonstrated that the new primer combination advantageously reduced differences between the times needed to achieve positive amplification results for numerous HIV-1 subtypes. FIG. 5A indicates that 3.4 minutes distinguished the times to achieve positive amplification results for the subtype B and O group templates when using primers that included the target-hybridizing sequences of SEQ ID NO:13 and SEQ ID NO:2. In contrast, FIG. 5B shows that this difference was reduced to only 1.3 minutes when the primers included the target-hybridizing sequences of SEQ ID NO:15 and SEQ ID NO:2. Additionally, differences between the times needed to achieve positive results for several subtypes also appeared to be minimized in reactions conducted using these primers. Despite these improvements, the amplification kinetics for the HIV-1 subtype E and subtype F templates appeared somewhat retarded compared with the amplification kinetics observed for the other samples.

It also was shown that, when paired with the primer of SEQ ID NO:2, the primer having the target-hybridizing sequence of SEQ ID NO:16 advantageously improved accuracy of quantitation for the HIV-1 O group template when compared with the combination of the primers having the target-hybridizing sequences of SEQ ID NO:2 and SEQ ID NO:13. Thus, the primer represents a preferred embodiment of the invention, particularly when paired with the primer of SEQ ID NO:2.

Finally, each of the primers identified by SEQ ID NOs:3-6 and 8-12 in Table 1, when paired with the primer of SEQ ID NO:15, and when compared with results obtained using the primer of SEQ ID NO:2 in combination with the primer of SEQ ID NO:15, behaved substantially equivalently. This pattern was demonstrated using the molecular beacon disclosed herein with the primers from Table 1 identified by SEQ ID NOs:3-9, and using the molecular torch disclosed herein with the primers from Table 1 identified by SEQ ID NO:5 (see below), SEQ ID NO:8, and SEQ ID NOs:10-12. For a reason that is unclear, equally good results were not achieved using the combination of primers having the target-hybridizing sequences of SEQ ID NO:7 and SEQ ID NO:15. Thus, any combination of the primer of SEQ ID NO:15 with any of the primers identified by SEQ ID NOs:3-6 and 8-12 represents a preferred combination of primers for amplifying HIV-1 nucleic acids. These combinations are particularly preferred when further combined with a molecular beacon hybridization probe, or with a molecular torch hybridization probe.

The foregoing procedures identified a primer combination that advantageously was capable of amplifying several HIV-1 subtypes with substantially equivalent kinetic profiles. Notably, HIV-1 subtypes E and F exhibited somewhat delayed amplification kinetics compared with the other targets used in the testing procedure. Having already modified the first- and second-strand primers, a different approach investigated the effects of modifying the detection probe used in the fluorescent monitoring protocol.

Example 4 describes procedures that identified oligonucleotide primers and a probe that yielded substantially equivalent amplification kinetics for all of the different HIV-1 variants.

EXAMPLE 4

Time-Dependent Monitoring of Amplicon Synthesis Using a Molecular Torch

Parallel amplification reactions were prepared essentially as described in the preceding Examples with the following modifications. A first-strand primer having the target-hybridizing sequence of SEQ ID NO:15 positioned downstream from a T7 promoter sequence (i.e., the promoter-primer of SEQ ID NO:19) was used in combination with a second-strand primer having the sequence SEQ ID NO:5. Additionally, a molecular torch having the sequence of SEQ ID NO:24 (i.e., having the target-hybridizing sequence given by SEQ ID NO:23) was substituted for the molecular beacon having the sequence of SEQ ID NO:22. The molecular torch was labeled at its 5' end with a fluorescein fluorophore, and at its 3' end with a DABCYL quencher moiety. Finally, in vitro transcripts representing HIV-1 subtypes A-C, E-F, G/A, H and O group were used as templates at 50 and 1,000 copies/reaction.

A standard curve was prepared from data obtained in trials conducted using the HIV-1 subtype B templates as illustrative HIV-1 M group standards at 50 and 1,000 copies/reaction. Reactions were carried out in replicates of six. The time required to effect detectable levels of amplification above background were plotted on the y-axis, and the number of copies/reaction of the standard plotted on the x-axis of the standard curve. The average time required to effect detectable levels of amplification in each reaction performed using the different HIV-1 subtypes was determined, and those time values used to establish average $\log_{10}$ copy values by comparison with the standard curve.

Figure 6A:
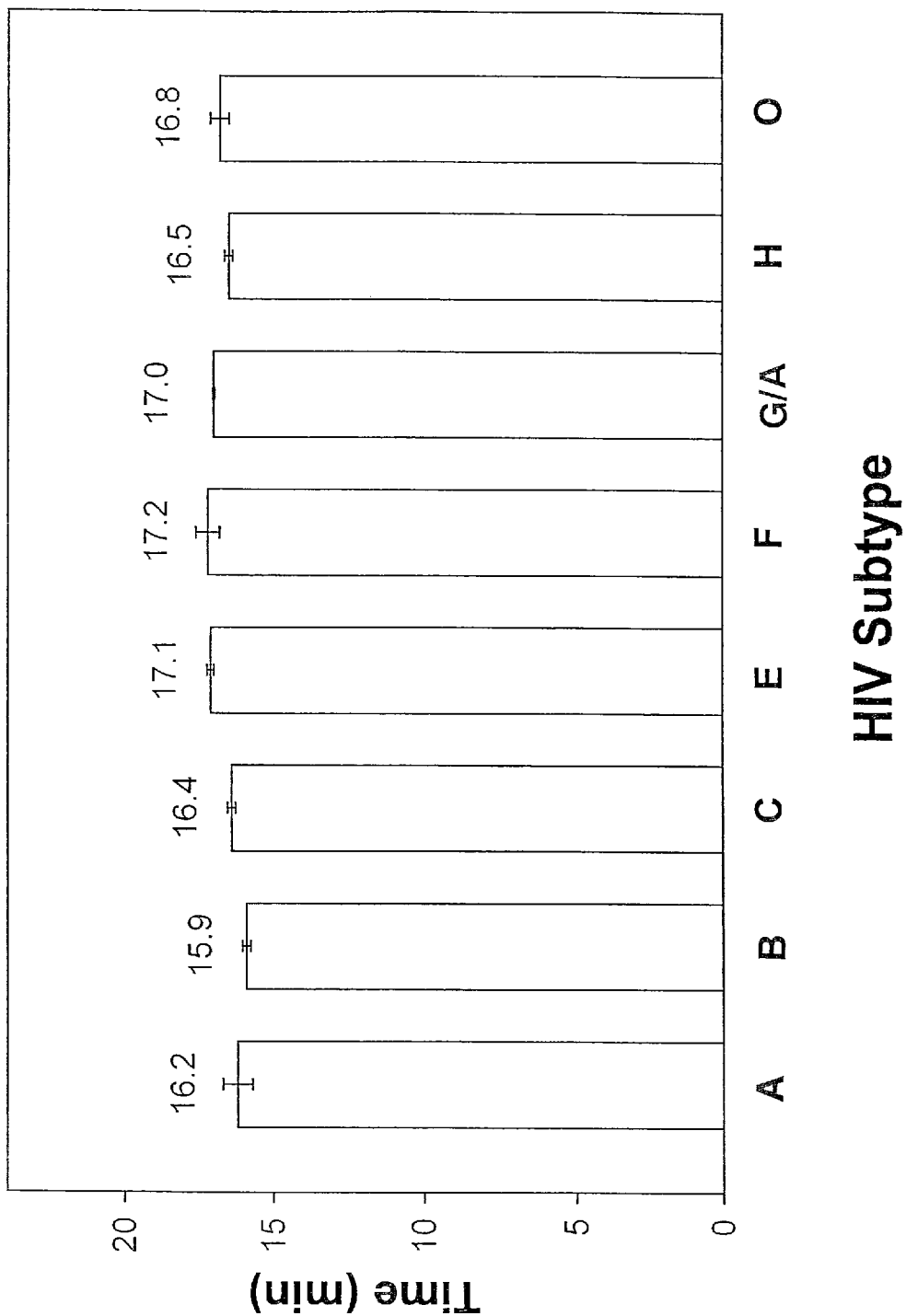
FIGS. 6A-6B show a series of bar graphs representing results for time-dependent amplification of numerous HIV-1 variants. Amplification primers had the target-hybridizing sequences of SEQ ID NO:5 and SEQ ID NO:15. The molecular torch hybridization probe used in the procedure had the target-hybridizing sequence of SEQ ID NO:23. Results are shown for amplification reactions conducted using 1,000 copies/reaction of the different HIV-1 subtypes.
Figure 6B:
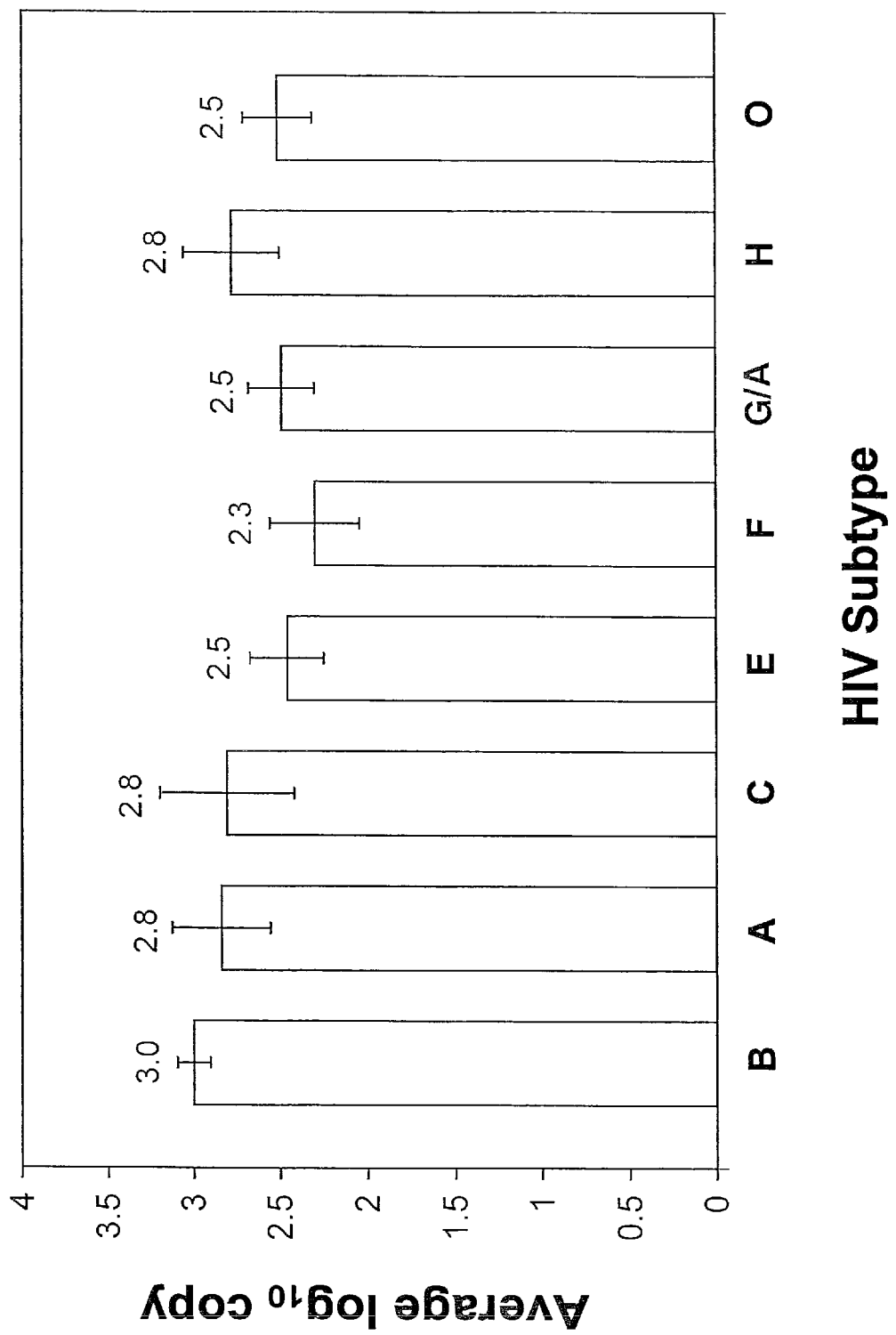

The results presented in FIGS. 6A-6B showed that all of the HIV-1 variants advantageously were amplified with substantially equal efficiency when using the specified combination of amplification primers, and when a molecular torch was substituted for the molecular beacon hybridization probe. The maximum difference among the times required to achieve positive amplification signals at the 1,000 copy/reaction level was reduced to only 1.3 minutes (0.7 $\log_{10}$ copies/reaction). Indeed, the difference between the determined number of HIV-1 subtype F templates (i.e., the species exhibiting the slowest amplification kinetics among the HIV-1 M group) did not exceed 0.7 $\log_{10}$ copies/reaction when reactions were initiated using 1,000 template copies/reaction. Likewise, the determined number of HIV-1 O group templates differed from the actual number of template copies/reaction by no more than 0.5 $\log_{10}$ copies/reaction when reactions were initiated using 1,000 template copies/reaction. The nature of real-time amplification systems, such as those disclosed herein, gives improved precision at increasing copy levels. Accordingly, differences between the actual number of HIV-1 template copies/reaction and the determined number of template copies/reaction will be less than 0.7 $\log_{10}$ copies/reaction for reactions carried out using greater than 1,000 copies/reaction of the HIV-1 subtype F species, and will be less than 0.5 $\log_{10}$ copies/reaction for reactions carried out using greater than 1,000 copies/reaction of the HIV-1 O group template.

The fact that the different HIV-1 subtypes gave more normalized time values in this procedure was attributed to the substitution of a molecular torch for a molecular beacon (as illustrated in the previous Example), because it was independently established that the second-strand primers of SEQ ID NO:2 and SEQ ID NO:5 performed essentially equivalently in the amplification reactions. Notably, the target-hybridizing sequences of SEQ ID NO:2 and SEQ ID NO:5 both conform to the consensus CCA-CAATTTTRAAAGAAAAGGG (SEQ ID NO:33). Further, our finding demonstrates that molecular torches can have advantages over molecular beacons when used as probes for real-time monitoring of isothermal amplification reactions, particularly when the target binding portion of the probe is required to hybridize to amplicons that are not fully complementary. As indicated above, the target-hybridizing sequence of the molecular torch was not fully complementary to the HIV-1 O group nucleic acid or amplicon, or to the nucleic acids or amplicons of HIV-1 M group subtypes A, E and F. Although not shown in the figure, all of the different subtypes were easily detected when present at the level of 50 copies/reaction, thereby demonstrating robustness of the amplification system.

Using a combination of primers and a probe that amplify HIV-1 M group and HIV-1 O group nucleic acids with substantially equal efficiency in a real-time amplification protocol, it is preferred to employ a polynucleotide of a single HIV-1 subtype as a calibration standard for assays capable of quantifying numerous different HIV-1 subtypes. For example, it is preferred to use an HIV-1 M group standard, such as a known amount of an HIV-1 subtype B nucleic acid, as a calibration standard. This HIV-1 M group nucleic acid standard can be used for establishing a point on a standard curve, and the resulting standard curve can be used for quantifying both HIV-1 M group and HIV-1 O group nucleic acids. Of course, it is also possible to employ a collection of HIV-1 M group standards, each having a different known amount of HIV-1 M group nucleic acids, to establish several points on a standard curve, and to use the resulting standard curve for quantifying the various HIV-1 M group and O group nucleic acids. Alternatively, instead of using the HIV-1 M group nucleic acid standard, HIV-1 O group standards can be employed instead. In this instance known amounts of an HIV-1 O group nucleic acid are employed as standards to create a standard curve by amplifying the nucleic acids using a combination of amplification primers and hybridization probe that amplify the HIV-1 M group and HIV-1 O group nucleic acids with substantially equal efficiencies. The resulting standard curve can be used for quantifying both HIV-1 O group and M group nucleic acids. It is even contemplated that a chimeric standard nucleic acid which is not strictly an HIV-1 M group nucleic acid or an HIV-1 O group nucleic acid could be used as a standard for quantifying both HIV-1 M group and O group nucleic acids.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A composition comprising an oligonucleotide primer, the base sequence of said oligonucleotide primer consisting of SEQ ID NO:19.

2. The composition of claim 1, further comprising a reverse transcriptase enzyme, and deoxyribonucleotide triphosphates.

3. The composition of claim 2, wherein the reverse transcriptase enzyme is MMLV reverse-transcriptase.

4. The composition of claim 2, further comprising ribonucleotide triphosphates.

5. The composition of claim 4, further comprising T7 RNA polymerase.

* * * * *

SEQUENCE LISTING

<160> NUMBER OF SEQ ID NOS: 33

<210> SEQ ID NO 1
<211> LENGTH: 19
<212> TYPE: DNA
<213> ORGANISM: Human immunodeficiency virus type 1

<400> SEQUENCE: 1
acagcagtac aaatggcag                                                  19

<210> SEQ ID NO 2
<211> LENGTH: 22
<212> TYPE: DNA
<213> ORGANISM: Human immunodeficiency virus type 1

<400> SEQUENCE: 2
ccacaatttt aaaagaaaag gg                                              22

<210> SEQ ID NO 3
<211> LENGTH: 22
<212> TYPE: DNA
<213> ORGANISM: Human immunodeficiency virus type 1

<400> SEQUENCE: 3
ccacaatttt aagagaaaag gg                                              22

<210> SEQ ID NO 4
<211> LENGTH: 22
<212> TYPE: DNA
<213> ORGANISM: Human immunodeficiency virus type 1

<400> SEQUENCE: 4
ccacaatttt agaagaaaag gg                                              22

<210> SEQ ID NO 5
<211> LENGTH: 22
<212> TYPE: DNA
<213> ORGANISM: Human immunodeficiency virus type 1

<400> SEQUENCE: 5
ccacaatttt gaaagaaaag gg                                              22

<210> SEQ ID NO 6
<211> LENGTH: 22
<212> TYPE: DNA
<213> ORGANISM: Human immunodeficiency virus type 1

<400> SEQUENCE: 6
ccacaatttt aaaggaaaag gg                                              22

<210> SEQ ID NO 7
<211> LENGTH: 22
<212> TYPE: DNA
<213> ORGANISM: Human immunodeficiency virus type 1

<400> SEQUENCE: 7
ccacaatttg aaaagaaaag gg                                              22

<210> SEQ ID NO 8
<211> LENGTH: 22
<212> TYPE: DNA
<213> ORGANISM: Human immunodeficiency virus type 1

<400> SEQUENCE: 8

```
ccacagttttt aaaagaaaag gg                                              22

<210> SEQ ID NO 9
<211> LENGTH: 23
<212> TYPE: DNA
<213> ORGANISM: Human immunodeficiency virus type 1

<400> SEQUENCE: 9 ccacaattttt gaaagaaaag ggg                                             23

<210> SEQ ID NO 10
<211> LENGTH: 22
<212> TYPE: DNA
<213> ORGANISM: Human immunodeficiency virus type 1

<400> SEQUENCE: 10
ccacaatatt aaaagaaaag gg                                               22

<210> SEQ ID NO 11
<211> LENGTH: 30
<212> TYPE: DNA
<213> ORGANISM: Human immunodeficiency virus type 1

<400> SEQUENCE: 11
ccacaatttt aaaagagaag ggggattgg                                        30

<210> SEQ ID NO 12
<211> LENGTH: 30
<212> TYPE: DNA
<213> ORGANISM: Human immunodeficiency virus type 1

<400> SEQUENCE: 12
ccacaatttt aaaaggaaag ggggattgg                                        30

<210> SEQ ID NO 13
<211> LENGTH: 29
<212> TYPE: DNA
<213> ORGANISM: Human immunodeficiency virus type 1

<400> SEQUENCE: 13
agtttgtatg tctgttgcta ttatgtcta                                        29

<210> SEQ ID NO 14
<211> LENGTH: 29
<212> TYPE: DNA
<213> ORGANISM: Human immunodeficiency virus type 1

<400> SEQUENCE: 14
agtttgtgtg tctgttgctg ttatgtcta                                        29

<210> SEQ ID NO 15
<211> LENGTH: 29
<212> TYPE: DNA
<213> ORGANISM: Human immunodeficiency virus type 1

<400> SEQUENCE: 15
agtttgtatg tctgatgcta ttatgtcta                                        29

<210> SEQ ID NO 16
<211> LENGTH: 29
<212> TYPE: DNA
<213> ORGANISM: Human immunodeficiency virus type 1
```

-continued

<400> SEQUENCE: 16
agtttgtatg tctggtgcta ttatgtcta					29

<210> SEQ ID NO 17
<211> LENGTH: 55
<212> TYPE: DNA
<213> ORGANISM: Artificial Sequence
<220> FEATURE:
<223> OTHER INFORMATION: HIV-1 promoter-primer
<220> FEATURE:
<221> NAME/KEY: promoter
<222> LOCATION: (1)..(26)

<400> SEQUENCE: 17
aatttaatac gactcactat agggagagtt tgtatgtctg ttgctattat gtcta					55

<210> SEQ ID NO 18
<211> LENGTH: 55
<212> TYPE: DNA
<213> ORGANISM: Artificial Sequence
<220> FEATURE:
<223> OTHER INFORMATION: HIV-1 promoter-primer
<220> FEATURE:
<221> NAME/KEY: promoter
<222> LOCATION: (1)..(26)

<400> SEQUENCE: 18
aatttaatac gactcactat agggagagtt tgtgtgtctg ttgctgttat gtcta					55

<210> SEQ ID NO 19
<211> LENGTH: 55
<212> TYPE: DNA
<213> ORGANISM: Artificial Sequence
<220> FEATURE:
<223> OTHER INFORMATION: HIV-1 promoter-primer

<400> SEQUENCE: 19
aatttaatac gactcactat agggagagtt tgtatgtctg atgctattat gtcta					55

<210> SEQ ID NO 20
<211> LENGTH: 55
<212> TYPE: DNA
<213> ORGANISM: Artificial Sequence
<220> FEATURE:
<223> OTHER INFORMATION: HIV-1 promoter-primer

<400> SEQUENCE: 20
aatttaatac gactcactat agggagagtt tgtatgtctg gtgctattat gtcta					55

<210> SEQ ID NO 21
<211> LENGTH: 15
<212> TYPE: RNA
<213> ORGANISM: Artificial Sequence
<220> FEATURE:
<223> OTHER INFORMATION: HIV-1 molecular beacon target-hybridizing
      sequence
<220> FEATURE:
<221> NAME/KEY: misc_feature
<222> LOCATION: (1)..(15)
<223> OTHER INFORMATION: methoxy backbone
<220> FEATURE:
<221> NAME/KEY: modified_base
<222> LOCATION: (4)..(4)
<223> OTHER INFORMATION: I

<400> SEQUENCE: 21 uggngggguac agugc					15

```
<210> SEQ ID NO 22
<211> LENGTH: 23
<212> TYPE: RNA
<213> ORGANISM: Artificial Sequence
<220> FEATURE:
<223> OTHER INFORMATION: HIV-1 molecular beacon
<220> FEATURE:
<221> NAME/KEY: misc_feature
<222> LOCATION: (1)..(23)
<223> OTHER INFORMATION: methoxy backbone
<220> FEATURE:
<221> NAME/KEY: modified_base
<222> LOCATION: (7)..(7)
<223> OTHER INFORMATION: I

<400> SEQUENCE: 22
ccguggnggg uacagugcca cgg                                            23

<210> SEQ ID NO 23
<211> LENGTH: 14
<212> TYPE: RNA
<213> ORGANISM: Artificial Sequence
<220> FEATURE:
<223> OTHER INFORMATION: HIV-1 molecular torch target-hybridizing
      sequence
<220> FEATURE:
<221> NAME/KEY: misc_feature
<222> LOCATION: (1)..(14)
<223> OTHER INFORMATION: methoxy backbone
<220> FEATURE:
<221> NAME/KEY: modified_base
<222> LOCATION: (3)..(3)
<223> OTHER INFORMATION: I

<400> SEQUENCE: 23
ggnggguaca gugc                                                      14

<210> SEQ ID NO 24
<211> LENGTH: 20
<212> TYPE: RNA
<213> ORGANISM: Artificial Sequence
<220> FEATURE:
<223> OTHER INFORMATION: HIV-1 molecular torch
<220> FEATURE:
<221> NAME/KEY: misc_feature
<222> LOCATION: (1)..(20)
<223> OTHER INFORMATION: methoxy backbone
<220> FEATURE:
<221> NAME/KEY: modified_base
<222> LOCATION: (4)..(4)
<223> OTHER INFORMATION: I
<220> FEATURE:
<221> NAME/KEY: misc_feature
<222> LOCATION: (15)..(16)
<223> OTHER INFORMATION: Non-nucleotide C9 linker inserted between base
      positions 15-16

<400> SEQUENCE: 24
cggnggguac agugcccccg                                                20

<210> SEQ ID NO 25
<211> LENGTH: 23
<212> TYPE: RNA
<213> ORGANISM: Human immunodeficiency virus type 1

<400> SEQUENCE: 25
gcuggaauaa cuucugcuuc uau                                            23

<210> SEQ ID NO 26
<211> LENGTH: 23
```

```
<212> TYPE: RNA
<213> ORGANISM: Human immunodeficiency virus type 1

<400> SEQUENCE: 26
gcuggaauag cuucugcuuc uau                                          23

<210> SEQ ID NO 27
<211> LENGTH: 24
<212> TYPE: RNA
<213> ORGANISM: Human immunodeficiency virus type 1

<400> SEQUENCE: 27
ucugcugucc cuguaauaaa cccg                                         24

<210> SEQ ID NO 28
<211> LENGTH: 24
<212> TYPE: RNA
<213> ORGANISM: Human immunodeficiency virus type 1

<400> SEQUENCE: 28
ucugcugucc cugugauaaa cccg                                         24

<210> SEQ ID NO 29
<211> LENGTH: 940
<212> TYPE: DNA
<213> ORGANISM: Human immunodeficiency virus type 1

<400> SEQUENCE: 29
ggtaccagca cacaaaggaa ttggaggaaa tgaacaagta gataaattag tcagtgctgg    60
aatcaggaaa gtactatttt tagatggaat agataaggcc caagatgaac atgagaaata   120
tcacagtaat tggagagcaa tggctagtga ttttaacctg ccacctgtag tagcaaaaga   180
aatagtagcc agctgtgata atgtcagct  aaaaggagaa gccatgcatg gacaagtaga   240
ctgtagtcca ggaatatggc aactagattg tacacattta gaaggaaaag ttatcctggt   300
agcagttcat gtagccagtg gatatataga agcagaagtt attccagcag aaacagggca   360
ggaaacagca tattttcttt taaaattagc aggaagatgg ccagtaaaaa caatacatac   420
tgacaatggc agcaatttca ccggtgctac ggttaggggcc gcctgttggt gggcgggaat   480
caagcaggaa tttggaattc cctacaatcc ccaaagtcaa ggagtagtag aatctatgaa   540
taaagaatta agaaaatta  taggacaggt aagagatcag gctgaacatc ttaagacagc   600
agtacaaatg gcagtattca tccacaattt taaaagaaaa ggggggattg ggggtacag    660 tgcaggggaa agaatagtag acataatagc aacagacata caaactaaag aattacaaaa   720
acaaattaca aaaattcaaa attttcgggt ttattacagg gacagcagaa atccactttg   780
gaaaggacca gcaaagctcc tctggaaagg tgaaggggca gtagtaatac aagataatag   840
tgacataaaa gtagtgccaa gagaaaagc  aaagatcatt agggattatg gaaacagat    900 ggcaggtgat gattgtgtgg caagtagaca ggatgaggat                         940

<210> SEQ ID NO 30
<211> LENGTH: 26
<212> TYPE: DNA
<213> ORGANISM: Bacteriophage T7

<400> SEQUENCE: 30
aatttaatac gactcactat agggag                                       26

<210> SEQ ID NO 31
```

```
<211> LENGTH: 15
<212> TYPE: DNA
<213> ORGANISM: Human immunodeficiency virus type 1

<400> SEQUENCE: 31 tgggggggtac agtgc                                                       15

<210> SEQ ID NO 32
<211> LENGTH: 461
<212> TYPE: DNA
<213> ORGANISM: Human immunodeficiency virus type 1
<220> FEATURE:
<221> NAME/KEY: misc_feature
<222> LOCATION: (418)..(418)
<223> OTHER INFORMATION: n is a, c, g, or t

<400> SEQUENCE: 32
agtgggttca tagaagcaga agtgatacca gcagaaacag gacaagaaac tgcctacttc       60
ctgttaaaac tggctgcaag atggcctgtt aaagtaatac atacagacaa cgggcctaat      120
tttacaagta caactatgaa ggctgcatgt tggtgggcca acatcaaca tgagtttgga       180 ataccatata atccacaaag tcaaggagta gtagaagcca tgaataagga attaaaatca      240
attatacagc aggtgaggga ccaagcagaa cacttaagaa cagcagtaca aatggcagta      300
tttgttcaca attttaaaag aaaagggggg attgggggggt acactgcagg agaaaggata    360
atagacatat tagcatcaca aatacaaaca acagaattac aaaaacaaat tttaaaantt      420
cacaaatttc gggtctatta cagagacagc agagaccta t                           461

<210> SEQ ID NO 33
<211> LENGTH: 22
<212> TYPE: DNA
<213> ORGANISM: Human immunodeficiency virus type 1

<400> SEQUENCE: 33
ccacaatttt raaagaaaag gg                                                22
```